US008764766B2

(12) United States Patent
Fujimoto et al.

(10) Patent No.: US 8,764,766 B2
(45) Date of Patent: Jul. 1, 2014

(54) INSERTION DEVICE

(75) Inventors: Hideo Fujimoto, Nagoya (JP); Shigeru Miyachi, Nagoya (JP); Tomotaka Ohshima, Nagoya (JP); Yoshitaka Nagano, Iwata (JP)

(73) Assignees: National University Corporation Nagoya Institute of Technology, Aichi (JP); National University Corporation Nagoya University, Aichi (JP); NTN Corporation, Osaka (JP)

( * ) Notice: Subject to any disclaimer, the term of this patent is extended or adjusted under 35 U.S.C. 154(b) by 354 days.

(21) Appl. No.: 13/124,572

(22) PCT Filed: Oct. 9, 2009

(86) PCT No.: PCT/JP2009/067623
§ 371 (c)(1),
(2), (4) Date: Jul. 8, 2011

(87) PCT Pub. No.: WO2010/044377
PCT Pub. Date: Apr. 22, 2010

(65) Prior Publication Data
US 2011/0264038 A1  Oct. 27, 2011

(30) Foreign Application Priority Data
Oct. 15, 2008  (JP) .................................. 2008-266483

(51) Int. Cl.
*A61F 11/00*  (2006.01)
*G01L 1/04*  (2006.01)
(52) U.S. Cl.
USPC .................................... 606/108; 73/862.621
(58) Field of Classification Search
USPC ............ 604/95.01–95.04; 600/101, 102, 104, 600/106, 114, 118, 126; 606/108; 73/862.621
See application file for complete search history.

(56) References Cited

U.S. PATENT DOCUMENTS 3,120,845 A    2/1964  Horner
6,406,280 B1   6/2002  Pfeiffer et al.

(Continued)

FOREIGN PATENT DOCUMENTS

EP    1582139 A3    12/2005
EP    2000789 A4    3/2010

(Continued)

OTHER PUBLICATIONS

Extended European Search Report issued in European Patent Application No. 09820555.2 dated Aug. 6, 2012.

(Continued)

*Primary Examiner* — Matthew F Desanto
(74) *Attorney, Agent, or Firm* — McDermott Will & Emery LLP

(57) ABSTRACT

There is provided an insertion device allowing a doctor to alone perform an operation to insert a medical linear body. The insertion device, operated to insert a delivery wire (104) into a human body (131) through a blood vessel (132), includes a foot switch (41, 46) generating and outputting a signal to control starting/stopping a drive device (1) moving the delivery wire (104) in its longitudinal direction. Furthermore, the insertion device includes an insertion force sensor (60) operative to measure longitudinally compressive force exerted to the delivery wire (104), and a speaker (92) and a display (93) informing an operator of the compressive force measured by the insertion force sensor (60).

10 Claims, 12 Drawing Sheets

(56) References Cited

U.S. PATENT DOCUMENTS

| | | | |
|---|---|---|---|
| 7,276,044 B2 | 10/2007 | Ferry et al. | |
| 2006/0161043 A1* | 7/2006 | Neumann et al. | 600/114 |
| 2008/0103358 A1 | 5/2008 | Suzuki | |

FOREIGN PATENT DOCUMENTS

| | | | |
|---|---|---|---|
| JP | 08-506512 | | 7/1996 |
| JP | 11-276608 | | 10/1999 |
| JP | 2000-042116 | | 2/2000 |
| JP | 2001-157662 | | 6/2001 |
| JP | 2005-287673 | | 10/2005 |
| JP | 2008-185361 | | 8/2008 |
| JP | 2008-190910 A | | 8/2008 |
| NL | 1019350 C2 | | 5/2003 |
| WO | WO 93/20876 | * | 10/1993 |
| WO | WO 95/23558 | | 9/1995 |
| WO | WO 99/45994 | | 9/1999 |
| WO | WO 2007/096951 | * | 8/2007 |
| WO | WO 2007/096951 A1 | | 8/2007 |
| WO | WO 2007/111182 | * | 10/2007 |
| WO | WO-2007/111182 A1 | | 10/2007 |

OTHER PUBLICATIONS

Decision to Grant issued in Japanese Application No. 2008-266483 mailed Oct. 1, 2013, with English translation, 6 pages.

* cited by examiner

INSERTION DEVICE

RELATED APPLICATIONS

This application is the U.S. National Phase under 35 U.S.C. §371 of International Application No. PCT/JP2009/067623, filed on Oct. 9, 2009, which in turn claims the benefit of Japanese Application No. 2008-266483, filed on Oct. 15, 2008, the disclosures of which Applications are incorporated by reference herein.

TECHNICAL FIELD

The present invention relates to an insertion device used to insert a medical linear body into bodily vessels.

BACKGROUND ART

Recently, less invasive surgeries such as treatments using catheters have been performed. The treatments using catheters include a coil embolization treatment. The coil embolization treatment is a treatment using a coil to place it in a cerebral aneurysm to embolize it to prevent the cerebral aneurysm, which is a cause of subarachnoidal hemorrhage, from rupture. FIG. 13 schematically shows a medical instrument used in a coil embolization treatment.

FIG. 13 shows a medical instrument 100. In this instrument, a coil 101 formed of platinum is used for embolizing a cerebral aneurysm 133. Coil 101 is connected to a tip of a delivery wire 104. Delivery wire 104 is inserted in a catheter, which includes a parent catheter 103 serving as an outer tube and a child catheter 102 serving as an inner tube to provide a double lumen catheter. Child catheter 102 is hollowed and delivery wire 104 is inserted into the hollowed portion of child catheter 102. Delivery wire 104 is inserted in a Y connector 121, and child catheter 102 is inserted in a Y connector 111.

Delivery wire 104 is manipulated by a doctor at a holding portion 106 located in a vicinity of an entrance of Y connector 121. Catheter 102 is manipulated by another doctor at a holding portion 105 located in a vicinity of an entrance of Y connector 111. In other words, two doctors manipulate delivery wire 104 and child catheter 102, respectively, in the vicinities of the entrances of Y connectors 111 and 121.

Y connector 111, 121 has three connection ports. One is a port for connecting a catheter. Another is a port for receiving a catheter, a delivery wire or a similar linear body. The other is ports 112, 122 for introducing physiological saline, agents and the like.

Parent catheter 103 is inserted into a human body 131 through a blood vessel 132 and has a tip having reached a vicinity of cerebral aneurysm 133. Child catheter 102 is inserted in parent catheter 103, and advanced through a tip of parent catheter 103 into cerebral aneurysm 133. Child catheter 102 reaches cerebral aneurysm 133 and from child catheter 102 coil 101, which is thin and soft, is pushed out and thus embolizes cerebral aneurysm 133. Cerebral aneurysm 133 is thus prevented from rupture.

FIG. 14 is a flowchart of a procedure of a coil embolization treatment. The coil embolization treatment is generally performed in a procedure shown in FIG. 14. Initially in step (S10) the double lumen structure of two catheters (parent catheter 103 and child catheter 102) and a guide wire used to guide the catheters to a target site are inserted into a femoral artery. Child catheter 102 is inserted in parent catheter 103 and the guide wire is inserted in child catheter 102. Then in step (S20) child catheter 102 has a tip guided by the guide wire and thus placed in cerebral aneurysm 133.

Then in step (S30) the guide wire is pulled out of child catheter 102. Then, step (S40) is performed to insert delivery wire 104 having a tip with platinum coil 101 attached thereto in place of the guide wire into child catheter 102.

Then step (S50) is performed to place coil 101 in cerebral aneurysm 133. Then step (S60) is performed to connect an electrode to delivery wire 104 and also connect an electrode to a needle previously stuck in human body 131 and thereafter pass a current between delivery wire 104 and human body 131 via the electrodes. Coil 101 and delivery wire 104 are connected by an electrolytic material, and accordingly, the passed current separates coil 101 and delivery wire 104 and as a result coil 101 is placed in cerebral aneurysm 133.

Then, step (S70) is performed to draw delivery wire 104 out of child catheter 102. Then, step (S80) is performed to determine whether coil 101 closely fills cerebral aneurysm 133. If not, the control returns to step (S40) to insert into child catheter 102 delivery wire 104 having another coil 101 attached thereto. Steps (S40) to (S70) are repeated until coil 101 closely fills cerebral aneurysm 133.

If it is determined that coil 101 has closely filled cerebral aneurysm 133, then, step (S90) is performed to draw parent catheter 103 and child catheter 102 out of human body 131. The treatment of cerebral aneurysm 133 by coil embolization is thus completed.

FIG. 15 schematically shows a catheter operation performed to place a coil in a cerebral aneurysm. As shown in FIG. 15(a), when a coil 101 connected to the tip of delivery wire 104 is placed in cerebral aneurysm 133 to embolize cerebral aneurysm 133, coil 101 may unevenly be distributed in cerebral aneurysm 133 and have an increased density in a vicinity of the tip of child catheter 102. When child catheter 102 has its tip in an area 134 having the coil densely, inserting coil 101 into cerebral aneurysm 133 is accompanied by increased resistance.

If delivery wire 104 is further advanced into blood vessel 132 with the increased insertion resistance, cerebral aneurysm 133, which renders the blood vessel's wall thin and fragile, may rupture. Accordingly, when that coil 101 is inserted with large insertion resistance is detected, the doctor who is manipulating delivery wire 104 temporarily stops inserting delivery wire 104.

Furthermore, the doctor who manipulates child catheter 102 retracts child catheter 102. More specifically, as shown in FIG. 15(b), the doctor who manipulates child catheter 102 moves child catheter 102 in a direction DR1 to draw the catheter out of blood vessel 132. Thereafter, the doctor who manipulates child catheter 102 again advances child catheter 102. More specifically, the doctor who manipulates child catheter 102 moves child catheter 102 in a direction DR2 to insert the catheter into blood vessel 132, as shown in FIG. 15(c), Child catheter 102 thus once retracted and again advanced has its tip repositioned and thus moved in cerebral aneurysm 133 to an area 135 having the coil less densely. When child catheter 102 has its tip with coil 101 around it less densely, coil 101 can be inserted into cerebral aneurysm 133 with smaller insertion resistance. In that condition, the doctor who manipulates delivery wire 104 resumes inserting delivery wire 104, i.e., coil 101 into cerebral aneurysm 133.

Thus a catheter treatment requires delicate control in manipulating catheters 102 and 103, delivery wire 104 and the like. Accordingly, it requires a skilled operator. Accordingly, to perform a catheter treatment with catheters 102 and 103, delivery wire 104 and the like improved in operability, some master-slave drive devices have been proposed (see Japanese Patent Laying-open Nos. 2000-042116 and 2001-157662 (Patent Documents 1 and 2, respectively, for example).

PRIOR ART DOCUMENTS

Patent Documents

Patent Document 1: Japanese Patent Laying-open No. 2000-042116
Patent Document 2: Japanese Patent Laying-open No. 2001-157662

SUMMARY OF THE INVENTION

Problems to be Solved by the Invention

The master-slave drive devices require an operation different from that performed to manually manipulate delivery wire 104 and catheters 102 and 103 or a similar linear body. Accordingly, the operator needs additional training. Furthermore, when the master-slave device is used, it is difficult to sense a delicate variation in a patient's pulse, blood vessel 132 and the like. Accordingly, it is preferable that the operator hold the linear body and manipulate it manually.

As has been set forth above, a conventional catheter treatment is performed with two doctors who hold child catheter 102 and delivery wire 104, respectively, working in liaison. If one of the doctors is skilled differently than the other or less skilled than the other, however, they may need more time for sufficient liaison. Furthermore, the doctors may be stressed out for liaison. Patent Document 1 describes a drive device with a linear body that is regarded as a catheter and a wire manipulated in a manner that is not different from the aforementioned, conventional surgery. Accordingly, the linear body needs to be manipulated by two doctors, and there is no means proposed to address this issue.

Furthermore, for a master-slave system, a problem has arisen that relates to a scale function for improved operability. The scale function varies a ratio of an amount of moving a linear body associated with a slave side to that of an operation associated with a master side in performing a delicate operation to provide a scale handleable by a human operator. If a scale value is set as N times, then an amount of movement associated with the slave side relative to an operation associated with the master side is a reciprocal of the scale value, i.e., 1/N, and at the time, the portion manipulated of the linear body associated with the master side will have a length of N times the amount of moving the linear body associated with the slave side. This requires preparing a portion to be manipulated that has a length in proportion to a maximum scale value. Such a portion to be manipulated, however, is unrealistic, since a catheter and a wire have a length of 1 meter to 2 meters. Furthermore, linear bodies that are manipulated are provided concentrically. Accordingly the inner linear body must be manipulated at a portion with the outer linear body absent, and the two operators or doctors will have a distance therebetween increased in proportion to the scale value, which renders the doctors' close liaison further difficult.

Furthermore, medical instruments must maintain hygiene, and it is desirable that a portion thereof that is brought into contact with a human body be disposable. To be disposable, it is required to be inexpensive. However, a master slave system, which has a large number of components, will be expensive.

The present invention has been made in view of the above issues and it mainly contemplates an insertion device used to insert a medical linear body into a bodily vessel, that is operable by a single doctor alone and also inexpensive and user-friendly.

Means for Solving the Problems

The present invention provides an insertion device for inserting a medical linear body into a bodily vessel, including: a drive device operative to move the medical linear body in a longitudinal direction thereof; a foot switch generating and outputting a signal to control starting/stopping the drive device; a measurement device operative to measure longitudinally compressive force exerted to the medical linear body; and a compressive force informing device informing an operator of the compressive force exerted to the medical linear body. The drive device includes: a torque generator; a driving roller providing rotational motion by a torque generated by the torque generator; a driven roller providing rotational motion as the driving roller rotates; a speed reducer posed between the torque generator and the driving roller, and receiving the torque from the torque generator, reducing the torque in speed, and outputting the torque reduced in speed; a casing having the torque generator and the speed reducer accommodated therein; and a rotary unit transmitting the torque from the speed reducer to the driving roller. The driving roller and the driven roller have a rotation surface and a rotation surface, respectively, cooperating to pinch the medical linear body. The casing has a hole receiving and passing the rotary unit therethrough. The hole has an inner circumferential surface provided with a seal in contact with an outer circumferential surface of the rotary unit and sealing an interior of the casing externally.

The medical linear body may be any of a catheter, a guide wire, and a delivery wire having a tip with a coil attached thereto for embolization.

Furthermore, the foot switch may include a foot switch for insertion and a foot switch for withdrawal. The foot switch for insertion may be operated to cause the drive device to operate to move the medical linear body in a direction to insert the medical linear body into the vessel, and the foot switch for withdrawal may be operated to cause the drive device to operate to move the medical linear body in a direction to withdraw the medical linear body from the vessel.

Furthermore, the measurement device may include: a sensor operative to sense a degree of a curvature of the medical linear body; and a conversion circuit converting the degree of the curvature of the medical linear body sensed by the sensor into the compressive force exerted to the medical linear body.

Furthermore, the compressive force informing device may include at least one of a visual instrument visually indicating the compressive force exerted to the medical linear body, and an audio instrument converting the compressive force exerted to the medical linear body into a sound corresponding thereto.

Furthermore, the torque generator may be an electric motor having a rotational speed controlled by voltage applied to the electric motor.

Furthermore, the insertion device may further include a rate control unit capable of adjusting a rate applied to cause the drive device to move the medical linear body.

Furthermore, the drive device may move the medical linear body at a rate of 1 mm/s to 4 mm/s in a direction to insert the medical linear body into the vessel.

Furthermore, the drive device may include a housing holding a medial instrument having a through hole capable of receiving and allowing the medical linear body to pass therethrough. The housing may have a lid member manually opened and closed as desired. The drive device may further include an elastic body attached to the lid member. The lid member may be provided with a lever operated to open/close the lid member. When the lid member is closed, the elastic body may press the lid member with elastic force, which may press and thus fix the lever. The lever may be elastically deformed to open the lid member.

The driving roller and the driven roller may have their respective rotation surfaces formed of an elastic material.

At least one of the driving roller and the driven roller may have the rotation surface provided with a groove, and the medical linear body may be disposed in the groove.

Effects of the Invention

The present insertion device allows an operator to hold a medical linear body by hand and manipulate the medical linear body manually and to also operate a foot switch with his/her foot to control the medical linear body to be moved in its longitudinal direction and stopped to allow the doctor to alone manipulate the medical linear body.

MODES FOR CARRYING OUT THE INVENTION

Hereinafter reference will be made to the drawings to describe the present invention in embodiments. In the figures, identical or corresponding components are identically denoted and will not be described repeatedly in detail.

Note that in the below described embodiments each component is not necessarily essential to the present invention unless otherwise indicated. It should also be noted that in the following embodiments when numbers, amounts and the like are referred to, the numbers, amounts and the like are only illustrative unless otherwise indicated, and the present invention is not necessarily limited thereto.

Figure 1:
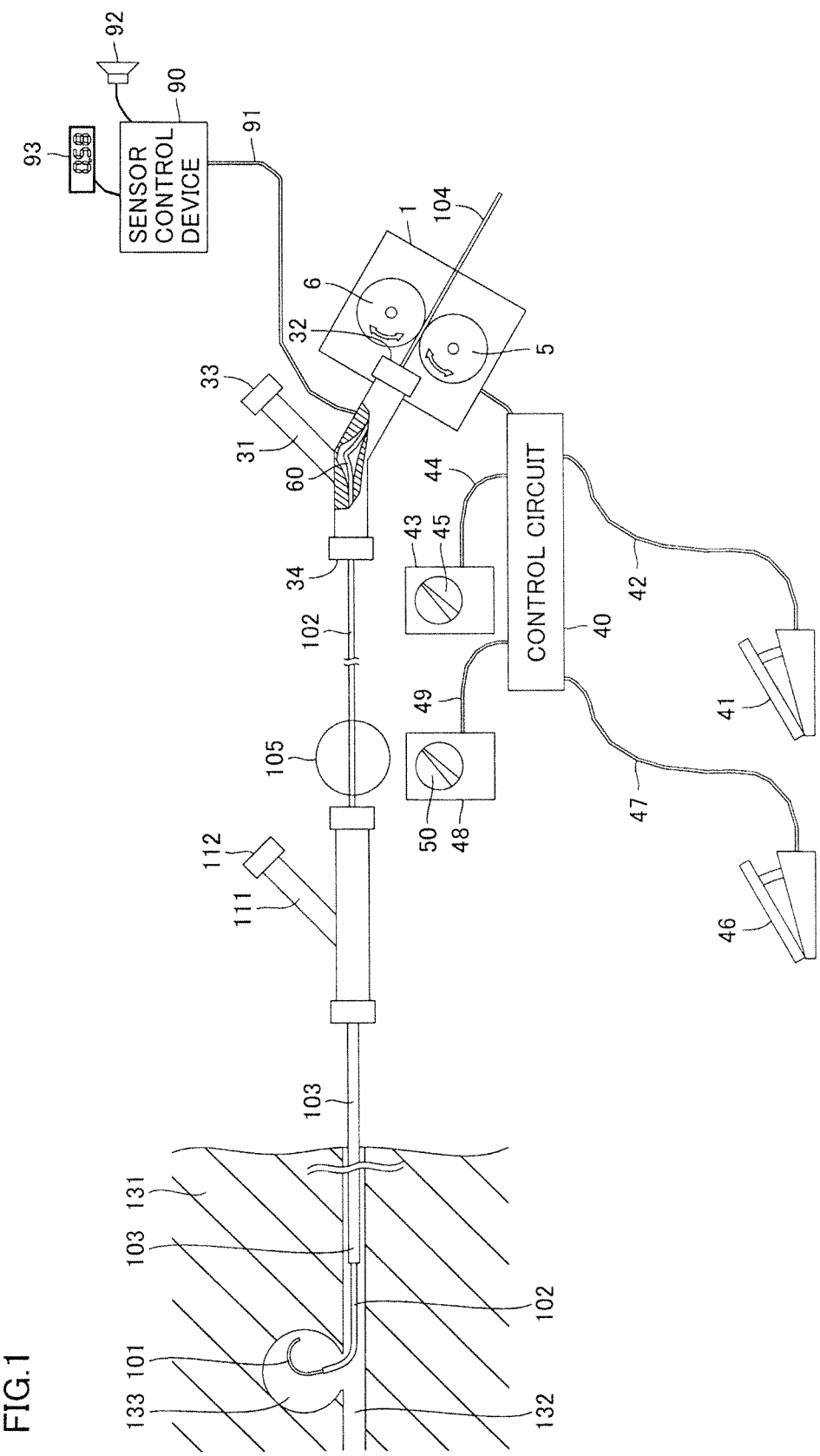
FIG. 1 schematically shows a configuration of an insertion device inserting a delivery wire into a blood vessel according to one embodiment of the present invention.

FIG. 1 schematically shows a configuration of an insertion device used to insert a delivery wire into a blood vessel according to one embodiment of the present invention. With reference to FIG. 1, an insertion device will be described that is used in a coil embolization treatment to insert into bodily blood vessel 132 delivery wire 104 inserted in catheters 102 and 103.

Figure 13:
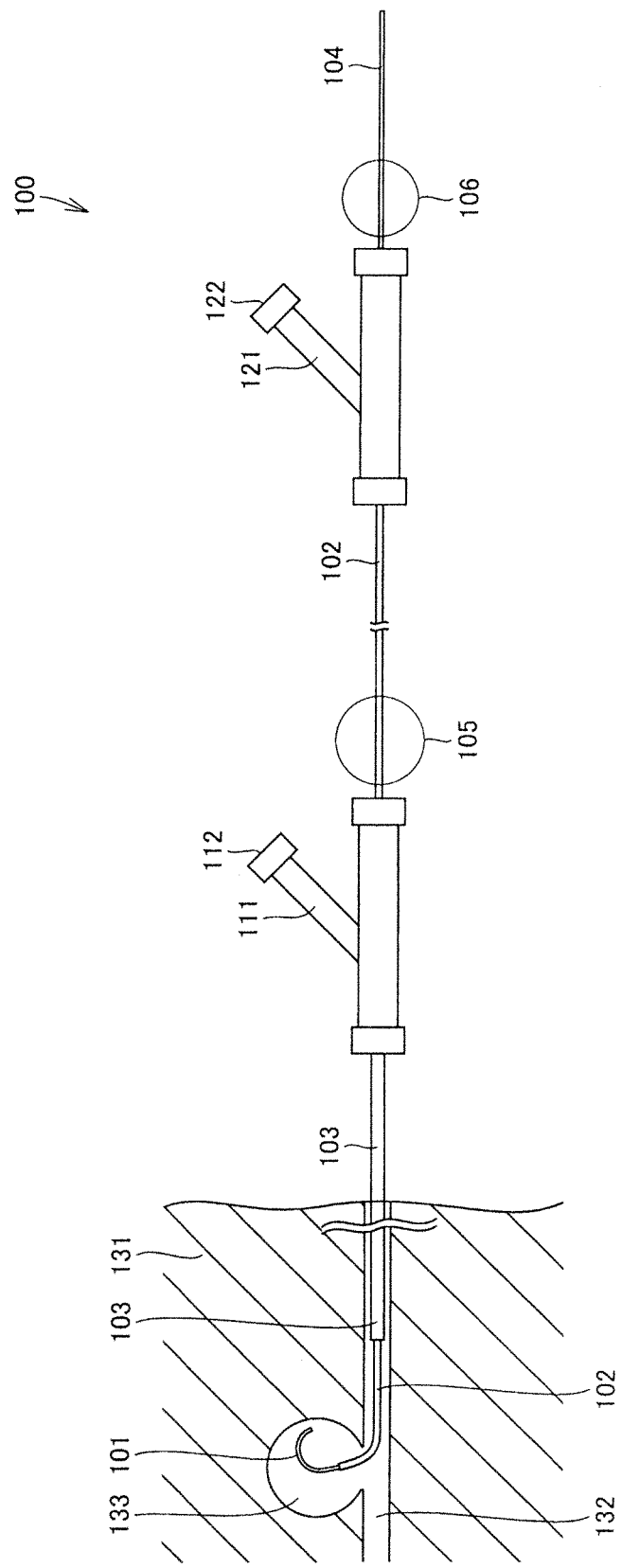
FIG. 13 schematically shows a medial instrument used in a coil embolization treatment.
Figure 14:
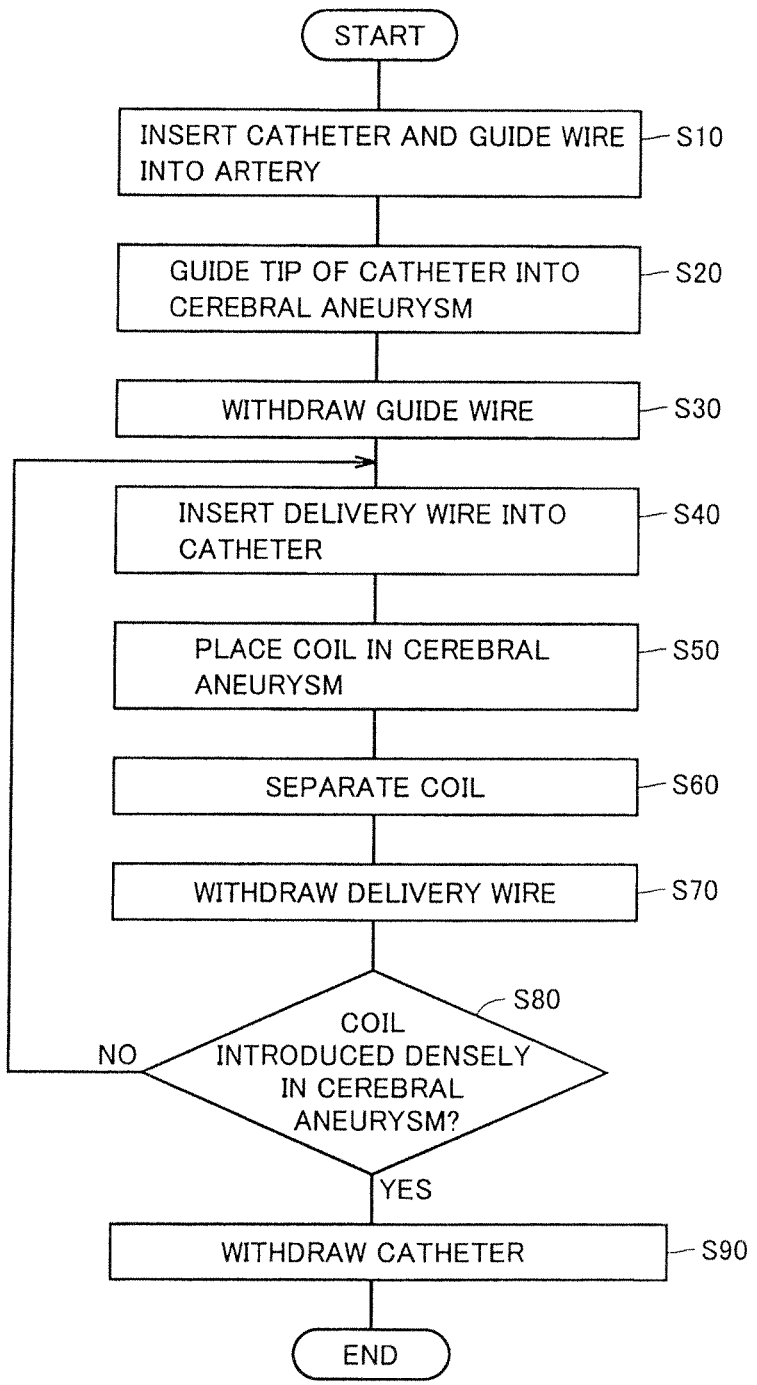
FIG. 14 is a flowchart of a procedure of a coil embolization treatment.
Figure 15:
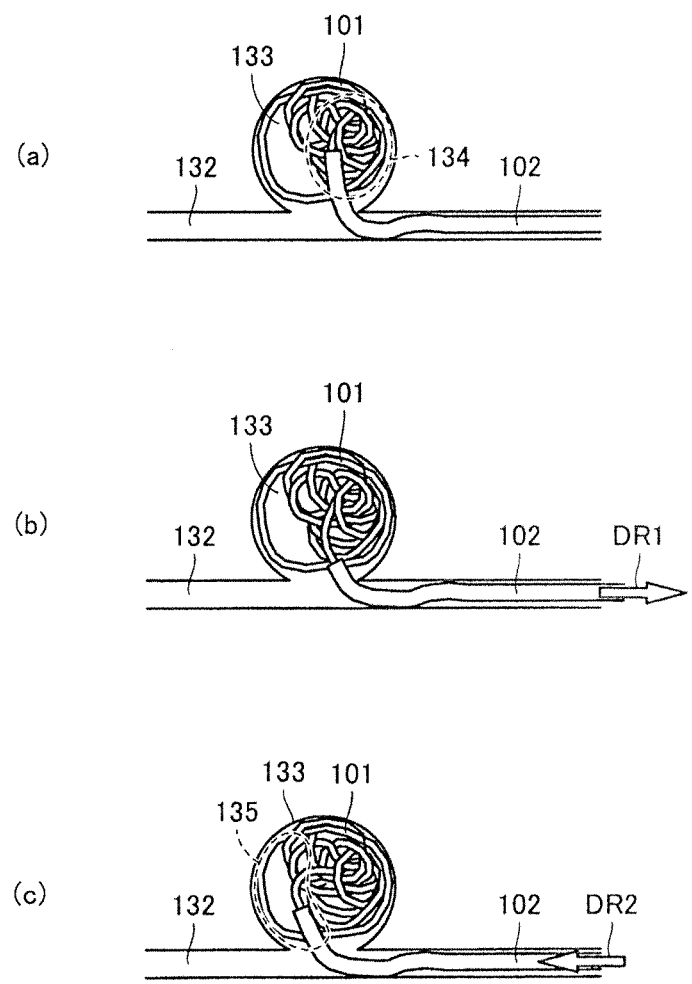
FIG. 15 schematically shows a catheter operation performed to place a coil in a cerebral aneurysm.

As shown in FIG. 1, a medical linear body implemented as delivery wire 104 is inserted in a Y connector 31. Delivery wire 104 has a tip with platinum coil 101 connected thereto to embolize cerebral aneurysm 133. Delivery wire 104 is inserted from a first input port 32 through Y connector 31 into child catheter 102 connected to an output port 34. Note that the configuration of the insertion device from the Y connector 31 output port 34 into human body 131 is identical to the FIG. 13 conventional medical instrument 100, and accordingly, it will not be described repeatedly.

The insertion device includes a drive device 1 moving delivery wire 104 in its longitudinal direction. Drive device 1 includes a driving roller 5 and a driven roller 6. Delivery wire 104 is pinched between a rotation surface of driving roller 5 and that of driven roller 6, and moved in its longitudinal direction as driving roller 5 rotates. Drive device 1 moves delivery wire 104 in its longitudinal direction, as controlled by a control circuit 40. Control circuit 40 has a foot switch 41 electrically connected thereto via a line 42 and operated for insertion, and a foot switch 46 electrically connected thereto via a line 47 and operated for withdrawal.

Figure 2:
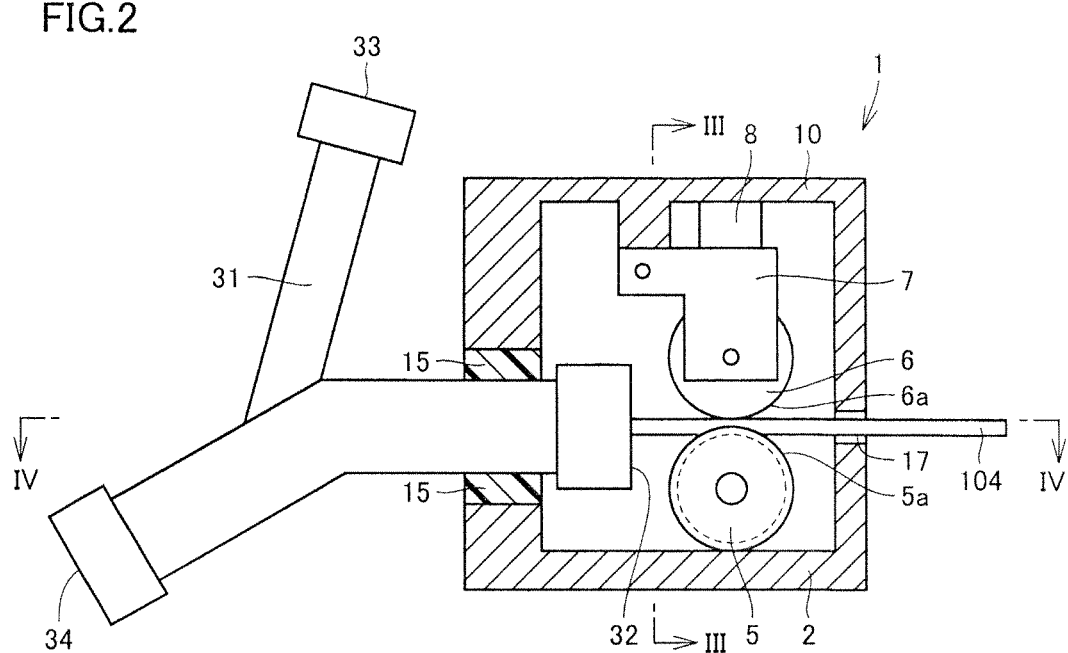
FIG. 2 is a schematic cross section of a drive device for a medical linear body.
Figure 3:
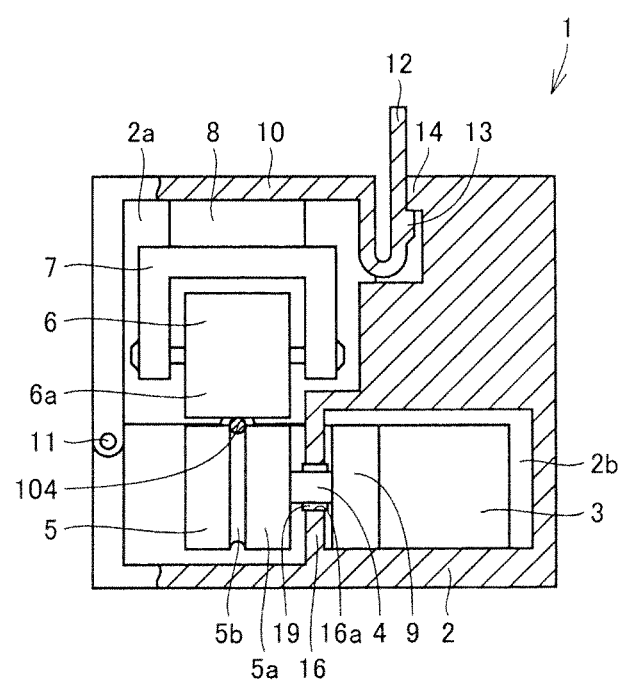
FIG. 3 is a partial schematic cross section of the drive device, taken along a line III-III shown in FIG. 2.
Figure 4:
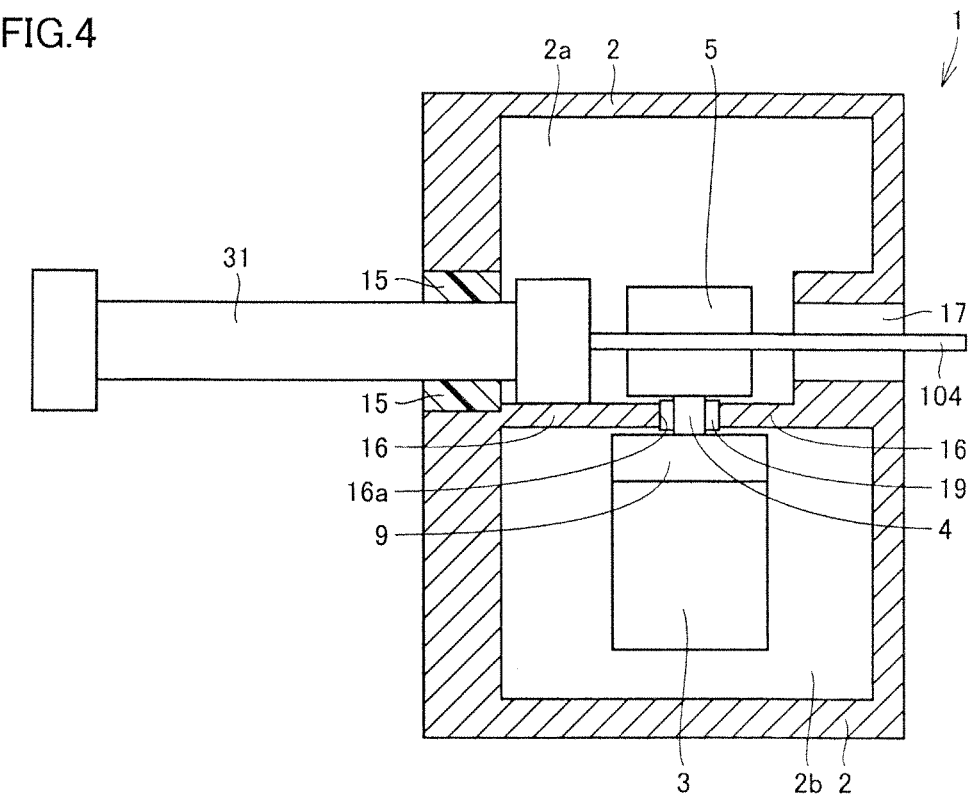
FIG. 4 is a schematic cross section of the drive device, taken along a line IV-IV shown in FIG. 2.
Figure 5:
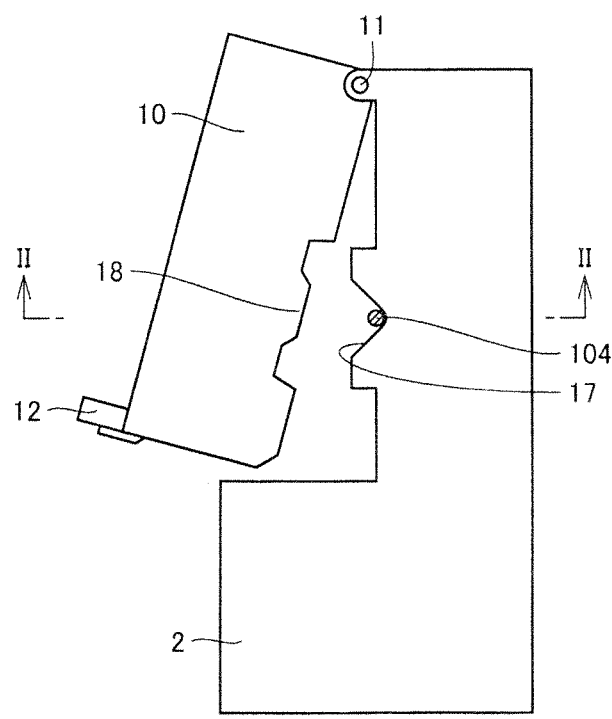
FIG. 5 is a side view of the drive device shown in FIGS. 2-4.

FIG. 2 is a schematic cross section of the drive device for a medical linear body. FIG. 3 is a partial schematic cross section of the drive device, taken along a line III-III shown in FIG. 2. FIG. 4 is a schematic cross section of the drive device, taken along a line IV-IV shown in FIG. 2. FIG. 5 is a side view of the drive device shown in FIGS. 2-4. With reference to FIGS. 2-5, how medical linear body (delivery wire 104) drive device 1 is configured will now be described. Note that FIG. 2 is a cross section of the drive device, taken along a line II-II shown in FIG. 5.

As shown in FIG. 2 to FIG. 5, drive device 1 includes a housing 2. Housing 2 has a lid member 10 opened and closed, as desired, as it pivots around a hinge 11 serving as a spindle. Drive device 1 has an internal space, formed such that it is surrounded by housing 2 and lid member 10, provided with a partition wall 16. Partition wall 16 sections the internal space of drive device 1 into a first space implemented as a large chamber 2a and a second space implemented as a small chamber 2b. Accommodated in small chamber 2b are a torque generator implemented as a motor 3 and a speed reducer 9 receiving a torque from motor 3, reducing the torque in speed and thus outputting it. Motor 3 is an electric motor converting electrical energy into mechanical energy.

Partition wall 16 has a hole 16a penetrating partition wall 16 in the direction of its thickness. Passed through hole 16a is a rotary unit implemented as a rotary shaft 4. Rotary shaft 4 transmits to driving roller 5 the torque generated by motor 3 and reduced in speed by speed reducer 9.

Small chamber 2b has an exterior formed of a casing formed of a portion of housing 2 and partition wall 16. The portion of housing 2 and partition wall 16 form a wall portion of the casing accommodating motor 3 and speed reducer 9 therein. As shown in FIGS. 3 and 4, the casing is provided in the form of a box of a rectangular parallelepiped, and partition wall 16 forms one wall surface of the casing and housing 2 forms three wall surfaces, i.e., bottom, ceiling and wall surfaces of housing 2. The casing has a portion configured of partition wall 16, which is provided with hole 16a receiving and passing rotary shaft 4 therethrough.

The partition wall 16 hole 16a has an inner circumferential surface provided with a seal 19. Seal 19 contacts the inner circumferential surface of hole 16a and also contacts an outer circumferential surface of rotary shaft 4. Seal 19 seals a gap between partition wall 16 and rotary shaft 4 and thus externally isolates the casing's interior or small chamber 2b. Small chamber 2b having motor 3 and speed reducer 9 accommodated therein communicates with large chamber 2a only through hole 16a. However, seal 19 sealing hole 16a renders large chamber 2a and small chamber 2b separate spaces. By providing seal 19 sealing hole 16a, small chamber 2b is provided as a sealed space. Seal 19 reduces/prevents liquid leaking from large chamber 2a through hole 16a into small chamber 2b.

Large chamber 2a has accommodated therein driving roller 5 providing rotational motion by the torque generated by motor 3 and transmitted via rotary shaft 4. Driving roller 5 is a feed roller attached to motor 3 via rotary shaft 4 and speed reducer 9 and is generally cylindrical. Speed reducer 9 is posed between motor 3 and driving roller 5. Rotary shaft 4 transmits a torque from speed reducer 9 to driving roller 5. Driving roller 5 has a cylindrical side surface, or a rotation surface 5a, having a feed groove 5b.

Furthermore, large chamber 2a has driven roller 6 accommodated therein opposite to the driving roller 5 rotation surface 5a. Driven roller 6, which is a pressing roller applying pressure to delivery wire 104, is generally cylindrical. Driven roller 6 has a cylindrical side surface, or a rotation surface 6a, which and the driving roller 5 rotation surface 5a cooperate to pinch delivery wire 104. The driving roller 5 rotation surface 5a and the driven roller 6 rotation surface 6a are positioned opposite to each other with delivery wire 104 posed therebetween. Delivery wire 104 is disposed between rotation surfaces 5a and 6a along feed groove 5b formed on driving roller 5 at rotation surface 5a.

When motor 3 is actuated and driving roller 5 accordingly provides rotational motion, driven roller 6 is driven by the rotation of driving roller 5 to provide rotational motion. Driving roller 5 and driven roller 6, rotating in opposite directions, respectively, move delivery wire 104 in its longitudinal direction. Delivery wire 104 is driven by driving roller 5. Motor 3 generating a torque, speed reducer 9 and rotary shaft 4 transmitting the torque, and driving roller 5 and driven roller 6 providing rotational motion are included in an actuator serving as a feed device moving delivery wire 104 in its longitudinal direction. The actuator pinches delivery wire 104 and moves it to feed it in its longitudinal direction. The actuator is accommodated in housing 2 at an internal space and held by housing 2.

It is desirable that the driving roller 5 rotation surface 5a and the driven roller 6 rotation surface 6a are formed such that when driven roller 6 is pressed against driving roller 5 to pinch delivery wire 104, delivery wire 104 can be protected from damage and also moved smoothly. For example, driving roller 5 and driven roller 6 can be formed of stainless steel and rotation surface 5a, 6a can be provided in the form of a coating of urethane resin or the like.

The driving roller 5 rotation surface 5a and the driven roller 6 rotation surface 6a formed of urethane resin or a similar elastic material allow a surface of delivery wire 104 to be brought into contact with rotation surfaces 5a, 6a over an area to cause an increased frictional force between rotation surfaces 5a, 6a and delivery wire 104. This frictional force can prevent delivery wire 104 moved with an increased compressive force exerted thereto in its longitudinal direction from slipping relative to rotation surfaces 5a, 6a. Furthermore, the driving roller 5 rotation surface 5a that has feed groove 5b contacts delivery wire 104 over an increased area. Feed groove 5b can also contribute to increasing the frictional force caused between rotation surfaces 5a, 6a and delivery wire 104.

While FIG. 3 shows feed groove 5b formed on driving roller 5 at rotation surface 5a by way of example, it is not limited to this configuration. The driving roller 5 rotation surface 5a may not be provided with a groove and instead have a smooth curved surface while the driven roller 6 rotation surface 6a may be provided with a feed groove receiving a linear body. Furthermore, rotation surfaces 5a, 6a may both have feed grooves, respectively. In other words, at least one of the driving roller 5 rotation surface 5a and the driven roller 6 rotation surface 6a having a groove receiving delivery wire 104 with delivery wire 104 having a surface in surface-contact with the groove's surface allows delivery wire 104 to contact rotation surfaces 5a, 6a over an increased area to cause an increased frictional force to effectively prevent delivery wire 104 from slipping.

Driven roller 6 is supported in an internal space of drive device 1, or large chamber 2a, by lid member 10 with a supporting member 7 supporting driven roller 6 rotatably and an elastic body 8 posed therebetween. Driven roller 6 is supported such that it is suspended from lid member 10. Elastic body 8 is attached to lid member 10. Driven roller 6 is supported by lid member 10 with elastic body 8 for example of rubber posed therebetween.

Lid member 10 has a lever 12 operated to open and close lid member 10. Lever 12 is elastically deformable. FIG. 3 shows lever 12 generally in the form of the letter U. Lever 12 is elastically deformable to decrease or increase the form of the letter U in width. Lever 12 has a projection 13. When projection 13 is engaged with housing 2 at an engagement portion 14, lever 12 is secured to housing 2.

Housing 2 and lid member 10 are provided with an elastic portion 15. As shown in FIG. 2, Y connector 31 is secured such that it is pinched by elastic portion 15 associated with housing 2 and elastic portion 15 associated with lid member 10. Housing 2 holds a medial instrument, or Y connector 31. Y connector 31 has one through hole extending therethrough from first input port 32 to reach output port 34. Delivery wire 104 is inserted into Y connector 31 through one through hole. Furthermore, Y connector 31 has another through hole extending therethrough from second input port 33 to reach output port 34.

Y connector 31 is a member secured at a securing portion of drive device 1. The securing portion has a form of a hole formed at a portion at which a sidewall of housing 2 and a sidewall of lid member 10 are aligned, and elastic portion 15 of rubber or the like provided on an inner circumference of the form of the hole. Drive device 1 is capable of securing the member to be secured, or Y connector 31, at the securing portion. Y connector 31 is sandwiched by elastic portion 15 attached to housing 2 and that attached to lid member 10, and is thus attached to the securing portion. Elastic portion 15 is held by housing 2.

The sidewalls of housing 2 and lid member 10, respectively, that are provided with the securing portion capable of securing Y connector 31 are opposite to another side wall of housing 2 and another sidewall of lid member 10, and a guide groove 17 is provided at a portion at which those other sidewalls are aligned. Guide groove 17 is provided at a portion where lid member 10 is aligned, at the other side wall of housing 2 opposite to the sidewall of housing 2 provided with elastic portion 15. Lid member 10 at the other sidewall has a raised portion 18 shaped to be fitted into guide groove 17. Guide groove 17 is formed by partially cutting out the other side wall of housing 2.

When lid member 10 is closed, raised portion 18 is fitted into guide groove 17. At the time, raised portion 18 and guide groove 17 define a space having a diameter slightly larger than the diameter of delivery wire 104 to allow delivery wire 104 to be passed therethrough. In other words, when lid member 10 is closed to attach delivery wire 104 and Y connector 31 integrally to the securing portion of drive device 1, delivery wire 104 is positioned by guide groove 17. Drive device 1 is provided with guide groove 17 that passes delivery wire 104 therethrough and serves as a guide portion positioning delivery wire 104.

Delivery wire 104 is placed in guide groove 17 at the deepest portion, which is formed substantially at a position where a virtual extension of a through hole of Y connector 31 intersects the other sidewalls of housing 2 and lid member 10 (typically, such that guide groove 17 extending through the other sidewall of housing 2 has the deepest portion extending in a direction matching a direction in which the Y connector 31 through hole extends).

When drive device 1 having the guide portion has lid member 10 closed, delivery wire 104 is positioned and set in position. Thus, when lid member 10 is closed, delivery wire 104 is set between driving roller 5 and driven roller 6 properly. This can prevent delivery wire 104 from being pinched between the aligned portions of lid member 10 and housing 2 and thus immobile or damaged or the like.

Guide groove 17 may be shaped in the from of the letter V, as shown in FIG. 5, or may be shaped in the form of the letter U, an arc, or a similar form having a curved surface having an appropriate curvature.

Drive device 1 has lid member 10 opened and closed in an operation, as will be described hereinafter. FIG. 2 and FIG. 3 show lid member 10 assuming a closed position. In this position, lever 12 is elastically deformed to reduce the form of the letter U in width to disengage projection 13 from engagement portion 14. Once projection 13 has been disengaged from engagement portion 14, lid member 10 is pivotable around hinge 11. In the FIG. 3 cross section, lid member 10 is pivoted around hinge 11 counterclockwise and thus opened. Lid member 10 has such a shape that lid member 10 can be opened manually by an operator holding and thus operating lever 12. Lever 12 can be elastically deformed to disengage projection 13 from engagement portion 14 to open lid member 10.

When lid member 10 is opened, elastic portion 15 attached to lid member 10 moves with lid member 10. Note that while lid member 10 is closed, elastic portion 15 exerts elastic force to a portion of the outer circumference of Y connector 31 to hold Y connector 31. Once lid member 10 has been opened, this elastic force is no longer exerted. This allows Y connector 31 to be moved manually. Furthermore, driven roller 6 also moves with lid member 10. Note that while the lid member 10 is closed, the driven roller 6 rotation surface 6a exerts force toward the driving roller 5 rotation surface 5a to press it. Once the lid member 10 has been opened, this force is relieved and delivery wire 104 having been pinched is no longer pinched and can thus be moved manually. As lid member 10 is moved, guide groove 17 has its perimeter partially opened, and delivery wire 104 can be moved not only in its longitudinal direction but also as desired.

As Y connector 31 and delivery wire 104 can both be moved manually, delivery wire 104 and Y connector 31 can be moved together while delivery wire 104 is inserted in a through hole of Y connector 31. Drive device 1 is provided with lid member 10 capable of opening a roller portion including driving roller 5 and driven roller 6, the securing portion securing Y connector 31, and guide groove 17. Opening lid member 10 allows delivery wire 104 inserted in Y connector 31 and Y connector 31 to be together removed from the securing portion securing Y connector 31. If power failure or similar emergency arises and drive device 1 is stopped, delivery wire 104 and Y connector 31 can integrally be removed manually.

On the other hand, when lid member 10 assuming an open position is pivoted around hinge 11, lid member 10 moves in a direction allowing it to be closed. In the FIG. 3 cross section, lid member 10 is pivoted around hinge 11 clockwise and thus closed. Lid member 10 can be closed manually by an operator holding and thus operating lever 12. When projection 13 of lever 12 impinges on engagement portion 14, lever 12 is elastically deformed so that its U letter form is decreased in width. Projection 13 slides on a surface of engagement portion 14 and thus passes by engagement portion 14.

Once projection 13 has passed by engagement portion 14, lever 12 elastically deforms so that its U letter form increases in width, and projection 13 engages with engagement portion 14. When lid member 10 is pushed down toward housing 2 to come close thereto, the movement of driven roller 6 and supporting member 7 attached to lid member 10 toward housing 2 is prevented by driving roller 5 axially supported by motor 3 secured to housing 2. Accordingly, elastic body 8 sandwiched between lid member 10 and supporting member 7 is elastically deformed.

Elastic body 8 elastically deformed exerts elastic force to lid member 10 as reaction, which presses lid member 10. The force exerted by elastic body 8 to lid member 10 causes projection 13 of lever 12 to closely contact engagement portion 14, and presses lever 12 against housing 2. Once lid member 10 has been closed, elastic body 8 presses lid member 10 with elastic force, which presses and thus fixes lever 12 against housing 2. Elastic body 8 exerts elastic force, which presses lever 12 against housing 2 and thus closes lid member 10.

When lid member 10 is open, Y connector 31 with delivery wire 104 through a through hole thereof can be assembled to elastic portion 15 of housing 2. When lid member 10 is closed in this condition, Y connector 31 is sandwiched by elastic portion 15 associated with housing 2 and elastic portion 15 associated with lid member 10. Furthermore, delivery wire 104 is pinched by the driving roller 5 rotation surface 5a and the driven roller 6 rotation surface 6a and also positioned in guide groove 17 so as to pass through housing 2 having guide groove 17. Delivery wire 104 and Y connector 31 are supported in drive device 1 by elastic portion 15, between the roller portion's driving roller 5 and driven roller 6, and by guide groove 17. Closing lid member 10 allows delivery wire 104 and Y connector 31 to be attached integrally to the securing portion of drive device 1.

Lid member 10 can be opened and closed manually by operating lever 12. As has been described previously, when lid member 10 is opened, delivery wire 104 and Y connector 31 can be integrally removed from the securing portion, and by closing lid member 10, delivery wire 104 and Y connector 31 can be integrally attached to the securing portion. In other words, according to the present embodiment, drive device 1 for delivery wire 104 allows delivery wire 104 and Y connector 31 to be integrally, detachably attached to the securing portion of drive device 1 manually.

Note that delivery wire 104 and Y connector 31 are detachably attachable to drive device 1 such that delivery wire 104 is inserted in a through hole of Y connector 31, i.e., integrally. However, it is not a requirement to attach delivery wire 104 and Y connector 31 integrally to drive device 1. More specifically, drive device 1 having a guide portion ensures that delivery wire 104 is positioned by the guide portion. As such, it is also possible that after lid member 10 is closed and Y connector 31 is attached to the securing portion, delivery wire 104 is inserted through the guide portion into drive device 1 and thus inserted through a through hole of Y connector 31. This can eliminate the necessity of constantly handling delivery wire 104 and Y connector 31 integrally, and thus enhance drive device 1 in operability.

Drive device 1 is applied to the FIG. 1 insertion device that inserts delivery wire 104 into a hollowed portion of child catheter 102 connected to a through hole of Y connector 31 and thus inserts delivery wire 104 into human body 131 through blood vessel 132. If power failure or similar emergency arises and drive device 1 is stopped, delivery wire 104 and Y connector 31 can integrally be removed manually. As Y connector 31 and delivery wire 104 can integrally be removed from drive device 1, child catheter 102 and delivery wire 104 can have their positional relationship unchanged before and after they are removed. This allows a treatment to be immediately, manually resumed without substantially changing the position of coil 101 in blood vessel 132, cerebral aneurysm 133 or the like.

The above described medical linear body drive device 1 includes an actuator moving delivery wire 104 in its longitudinal direction. The actuator includes motor 3, speed reducer 9 receiving a torque that is generated by motor 3, reducing the torque in speed and thus outputting it, driving roller 5 performing rotational motion by the torque transmitted from motor 3, and driven roller 6 performing rotational motion as the driving roller 5 rotates.

Thus, while driving roller 5 driving delivery wire 104 is rotated by motor 3, motor 3 has its rotational driving force transmitted via speed reducer 9 to driving roller 5. Operating speed reducer 9 to reduce a rotational driving force generated by motor 3 in rotational speed can increase a torque in proportion to a ratio in rotational speed of an output shaft of motor 3 and that of speed reducer 9, i.e., a speed reduction ratio. Operating speed reducer 9 to reduce rotational speed can increase a torque transmitted to driving roller 5 and increase a driving force moving delivery wire 104 in its longitudinal direction. This allows a miniature motor to be used to obtain desired force to drive delivery wire 104 and drive device 1 to be produced at a reduced cost.

For example, if delivery wire 104 is moved at a rate of 1 mm/s and driving roller 5 has a radius of 10 mm, then, driving roller 5 has a rotational speed of approximately 1 rpm (=1 mm/s divided by (10 mm×2π)×60 s). Obtaining this rotational speed of driving roller 5 such that motor 3 rotatable at a rotational speed larger than that of driving roller 5 is employed and speed reducer 9 is operated to reduce the rotational speed of the output shaft of motor 3 for output to driving roller 5, allows driving roller 5 to drive delivery wire 104 with an increased force.

When motor 3 drives delivery wire 104 and delivery wire 104 experiences resistance by an external frictional force or a similar external load, the resistive force will be a reciprocal of the speed reduction ratio. For example, when motor 3 is rotated at a relatively large speed reduction ratio of approximately 100 to 1000, a resistive force acting on delivery wire 104 relative to the rotational driving force of motor 3 can be ignored. Delivery wire 104 can thus be driven stably at a predetermined rate.

Note that delivery wire 104 may be moved in its longitudinal direction by any actuator that can move elongate delivery wire 104 in the direction in which it extends. Desirably, however, it is an actuator including motor 3 serving as an electric motor as described in the present embodiment. Drive device 1 including motor 3 as an electric motor and using a torque generated by motor 3 to move delivery wire 104 allows motor 3 to be controlled in rotational speed by increasing/decreasing, a voltage applied to motor 3.

Delivery wire 104 is moved at a rate determined in accordance with the rotational speed of motor 3. For example, for a practical range (equal to or smaller than the number of insertion force N), the voltage applied to motor 3 and the rate at which delivery wire 104 is moved have a linear relationship. Accordingly, previously preparing a table indicating the relationship between the voltage applied to motor 3 and the rate at which delivery wire 104 is moved allows a voltage applied to motor 3 to be varied in accordance with a rate at which delivery wire 104 is moved, as intended by the operator.

Thus, simply varying a voltage applied to motor 3 allows delivery wire 104 to be moved in its longitudinal direction at any desired rate. Thus, a simple configuration can be used to control a rate at which delivery wire 104 is moved. A sensor, such as an encoder, is not required to sense the rotational rate of driving roller 5, and drive device 1 can have a reduced number of components. Drive device 1 can thus be produced at a reduced cost and also be enhanced in reliability.

Furthermore, motor 3 and speed reducer 9 are accommodated in small chamber 2b having an interior connected to an exterior through hole 16a receiving and passing rotary shaft 4 therethrough, and hole 16a is internally provided with seal 19 in contact with an inner circumferential surface of hole 16a and an outer circumferential surface of rotary shaft 4.

When delivery wire 104 is a delivery wire or a guide wire or the like inserted into a human body, drive device 1 needs to be configured to facilitate cleaning and disinfecting large chamber 2a having driving roller 5 and driven roller 6 accommodated therein to pinch and drive delivery wire 104. Furthermore a surgical operation is performed using physiological saline, drug and the like injected through the Y connector 31 second input port 33. Accordingly, it is necessary to waterproof motor 3, speed reducer 9 and the like. Seal 19 that can isolate the interior of small chamber 2b from large chamber 2a can prevent liquid from entering from large chamber 2a to small chamber 2b. Seal 19 posed between rotary shaft 4 and partition wall 16 can be formed of an elastic material such as a resin material represented by silicone resin.

As seal 19 is provided, rotary shaft 4 rotated has its outer circumferential surface sliding in contact with seal 19. Accordingly, an increased torque is required to rotate rotary shaft 4. In the present embodiment, however, the torque generated by motor 3 is transmitted via speed reducer 9 through rotary shaft 4 to driving roller 5, and driving roller 5 receives an increased torque. Accordingly, a frictional resistance caused as rotary shaft 4 slides relative to seal 19 can be ignored as seen from motor 3. Delivery wire 104 can thus be driven stably at a predetermined rate.

Returning to FIG. 1, the insertion device includes a foot switch. The foot switch is stepped on by the operator to generate a signal to control starting/stopping drive device 1. The foot switch allows an operator who manipulates child catheter 102 by hand to switch on/off drive device 1 without using his/her hand(s). The foot switch includes foot switches 41 and 46 for insertion and withdrawal, respectively. Foot switch 41 is connected to control circuit 40 by line 42. Foot switch 46 is connected to control circuit 40 by line 47.

When foot switch 41 is stepped on, a micro-switch incorporated therein is pressed and drive device 1 is operated to move delivery wire 104 in a direction to insert delivery wire 104 into blood vessel 132. More specifically, driving roller 5 is rotated to drive delivery wire 104 in a direction to advance delivery wire 104, i.e., a direction to insert delivery wire 104 into child catheter 102. An operation is thus performed to insert coil 101 into cerebral aneurysm 133.

When foot switch 46 is stepped on, a micro-switch incorporated therein is pressed and drive device 1 is operated to move delivery wire 104 in a direction to withdraw delivery wire 104 from blood vessel 132. More specifically, driving roller S is rotated inversely to drive delivery wire 104 in a direction to retract delivery wire 104, i.e., a direction to withdraw delivery wire 104 from child catheter 102. An operation is thus performed to withdraw from blood vessel 132 delivery wire 104 having a tip with coil 101 attached thereto.

When foot switch 41, 46 is stepped off, a return spring exerts elastic force to release the incorporated micro-switch having been pressed. As a result, delivery wire 104 no longer receives driving force acting thereon and thus stops.

A doctor who employs this insertion device to perform a coil embolization treatment can press with his/her left hand Y connector 111 having child catheter 102 inserted therein and hold and manipulate child catheter 102 with his/her right hand at holding portion 105 located in a vicinity of an entrance of Y connector 111. Furthermore, the same doctor can operate foot switch 41 and foot switch 46 with his/her foot to insert delivery wire 104 into child catheter 102 and thus insert coil 101 into cerebral aneurysm 133. More specifically, catheter 102 and delivery wire 104 can be manipulated by a single doctor alone.

The present insertion device thus allows a single doctor to alone perform a treatment placing coil 101 in cerebral aneurysm 133 to embolize cerebral aneurysm 133 with the coil. Conventionally, two doctors perform a coil embolization treatment. The present insertion device allows only a single doctor to alone perform the treatment. This can eliminate the necessity of two doctors cooperating in liaison to perform the treatment and can thus alleviate their stress otherwise accompanying their liaison.

Child catheter 102 is manipulated, as conventional, i.e., held by a doctor at holding portion 105 and thus manually manipulated. On the other hand, drive device 1 is provided to move delivery wire 104, and delivery wire 104 is driven by drive device 1. Drive device 1 is started/stopped as controlled by operating foot switch 41 or foot switch 46. The doctor who manipulates child catheter 102 by hand operates the foot switches with his/her foot.

The insertion device operated to insert delivery wire 104 to allow a single doctor to alone perform a coil embolization treatment can thus be simply configured. Accordingly, the insertion device can be produced at a reduced cost and also enhanced in reliability. Foot switch 41 used to advance delivery wire 104 to insert it and foot switch 46 used to retract delivery wire 104 to withdraw it are provided separately. Delivery wire 104 is thus less erroneously inserted/withdrawn. The insertion device can further be enhanced in reliability.

Control circuit 40 shown in FIG. 1 has an insertion rate control unit 43 and a withdrawal rate control unit 48 electrically connected thereto via a line 44 and a line 49, respectively. Insertion rate control unit 43 and withdrawal rate control unit 48 have volume switches 45 and 50, respectively, attached thereto to allow drive device 1 to move delivery wire 104 at an adjustable rate.

Volume switches 45 and 50 provided to the rate control unit (insertion rate control unit 43 and withdrawal rate control unit 48) can be operated to allow delivery wire 104 to be inserted/withdrawn at an increased/decreased rate. When a doctor who performs a coil embolization treatment alone inserts child catheter 102 into Y connector 11, the doctor holds Y connector 111 with his/her left hand. When the doctor wishes to insert or withdraw delivery wire 104 at an increased or decreased rate, the doctor operates the rate control unit's (i.e., the insertion rate control unit 43 or withdrawal rate control unit 48) volume switches 45 and 50 with his/her right hand. Delivery wire 104 can thus be moved in its longitudinal direction at a controlled rate.

The rate control unit that allows delivery wire 104 to be moved at a variable rate allows a coil embolization treatment to be performed with delivery wire 104 inserted into blood vessel 132 continuously. That is, coil 101 attached to the tip of delivery wire 104 can be continuously inserted into cerebral aneurysm 133. This can prevent coil 101 from being in contact with a wall of cerebral aneurysm 133 (an aneurysmal wall) stationarily and thus causing static friction with the aneurysmal wall, and consequently being inserted with an increased insertion resistance caused. In other words, coil 101 can be inserted into cerebral aneurysm 133 without delivery wire 104 experiencing a disadvantageously varying longitudinally compressive force.

Furthermore, the rate control unit that allows delivery wire 104 to be moved at a finely adjusted rate allows delivery wire 104 to be moved at a reduced rate for example in placing coil 101 in cerebral aneurysm 133 or requiring a similar careful operation to further ensure the operation.

When drive device 1 is used to insert delivery wire 104 into cerebral aneurysm 133, the rate control unit can be set to allow an insertion rate to be adjustable in a range of 1 mm/s to 4 mm/s for the following reason:

Initially, doctors each insert a coil into a simulated cerebral aneurysm of silicone resin at rates, as shown in table 1. As each doctor delivers the coil with his/her fingers reciprocated, the coil is not delivered at a fixed rate, however, a coil insertion rate mean value is calculated from the coil's length and its insertion time.

TABLE 1

|  | Doctor A | Doctor B |
| --- | --- | --- |
| Coil | 4.44 | 1.78 |
| Insertion | 4.29 | 2.00 |
| Rate | 2.86 | 4.29 |
| [mm/s] | 1.48 | 1.67 |
|  | 3.03 | 3.33 |
|  | 2.86 | 1.67 |
|  | 3.33 | 1.58 |
| Mean Rate | 3.18 | 2.33 |
| Min. Rate | 1.48 | 1.58 |
| Max. Rate | 4.44 | 4.29 |

Table 1 shows a result of an insertion rate provided when two doctors A and B use a variety of types of coils and insert them into the simulated cerebral aneurysm. The insertion rate is approximately 1.5 to 4.4 mm/s. It is believed that when drive device 1 is operated to insert delivery wire 104 with a maximum insertion rate excessively increased, it is difficult to do so in liaison with operating child catheter 102. Accordingly, delivery wire 104 is appropriately inserted with a maximum rate in a vicinity of a maximum value of an average rate obtained when each doctor inserts the coils by hand, as shown in table 1, i.e., 4.0 mm/s.

Figure 6:
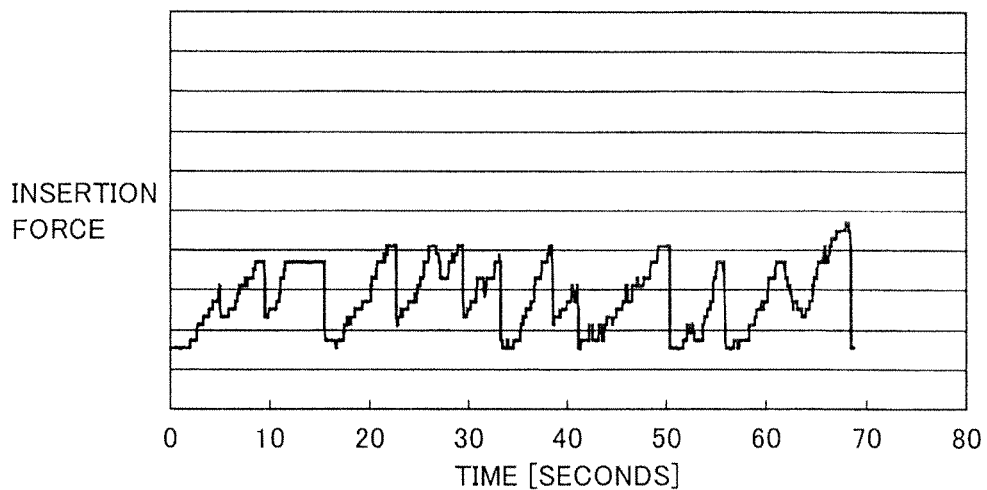
FIG. 6 is a graph representing variation of insertion force caused as a coil is inserted into a simulated cerebral aneurysm at a rate of 0.5 mm/s.
Figure 7:
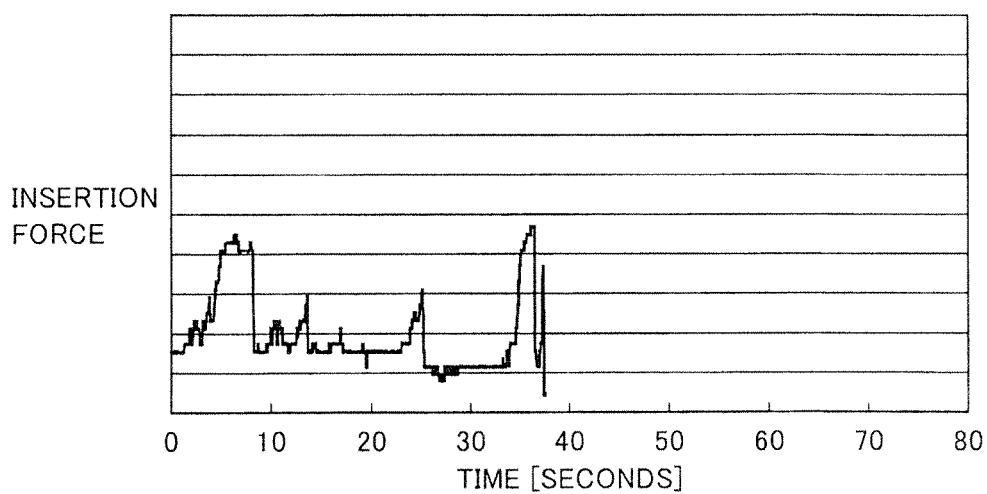
FIG. 7 is a graph representing variation of insertion force caused as the coil is inserted into the simulated cerebral aneurysm at a rate of 1.0 mm/s.

Furthermore, a test was conducted using a motor to insert a coil into a simulated cerebral aneurysm of silicone resin at a fixed rate to examine insertion force. Insertion force as referred to herein indicates longitudinally compressive force exerted to a linear body or a coil, that is required to move the coil in a direction to insert the coil into the simulated cerebral aneurysm. FIG. 6 is a graph representing variation of insertion force caused as a coil is inserted into the simulated cerebral aneurysm at a rate of 0.5 mm/s. FIG. 7 is a graph representing variation of insertion force caused as the coil is inserted into the simulated cerebral aneurysm at a rate of 1.0 mm/s. The FIGS. 6 and 7 graphs each have an axis of abscissas representing elapse of time (unit: second) and an axis of ordinates representing insertion force as represented relatively. When FIGS. 6 and 7 are compared, FIG. 6's insertion rate of 0.5 m/s results in a larger mean insertion force value.

Figure 8:
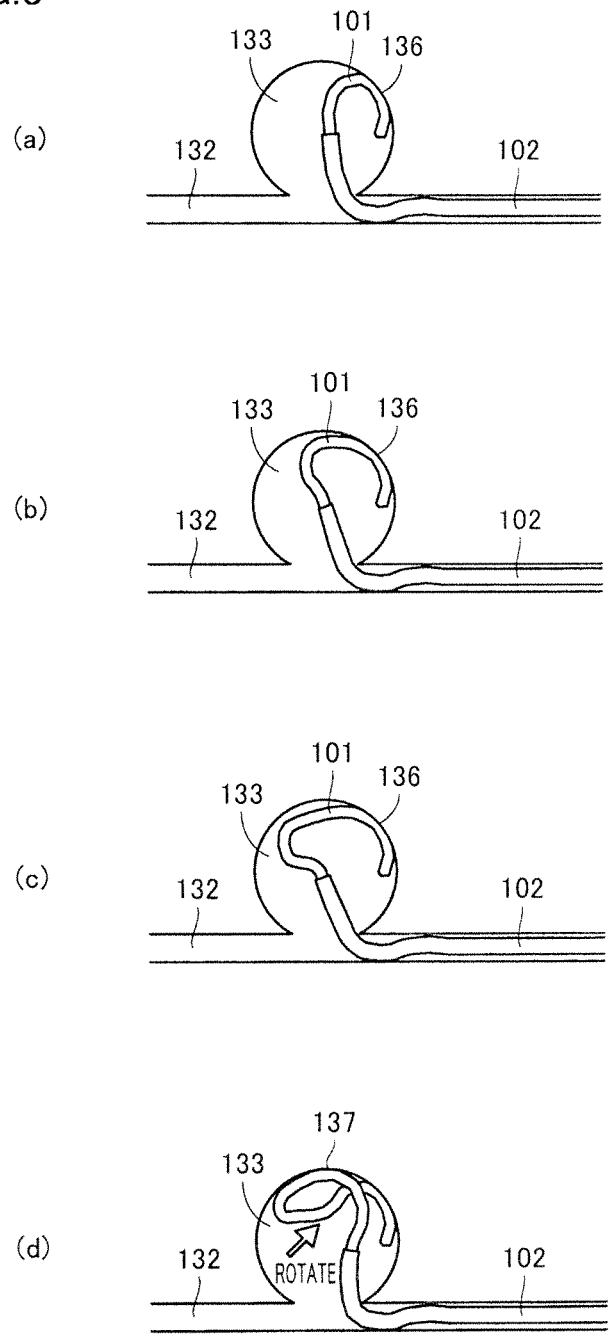
FIG. 8 schematically shows how a coil behaves in a simulated cerebral aneurysm when the coil is inserted into the simulated cerebral aneurysm at a rate of 0.5 mm/s.

FIG. 8 schematically shows how a coil behaves in a simulated cerebral aneurysm when the coil is inserted in the simulated cerebral aneurysm at a rate of 0.5 mm/s. As shown in FIG. 8(*a*), when coil 101 is inserted via child catheter 102 into cerebral aneurysm 133, coil 101 partially contacts the wall portion of cerebral aneurysm 133 (an aneurysmal wall) at a point indicated as a restraint point 136. Coil 101 is stationary at restraint point 136 relative to the aneurysmal wall and static frictional force is caused between coil 101 and the aneurysmal wall. As static frictional force is caused and frictional force is increased between coil 101 and the aneurysmal wall, coil 101 is restrained at restraint point 136 relative to the aneurysmal wall. In that condition, further inserting coil 101 flexes coil 101 at an exit of child catheter 102, as shown in FIG. 8(*b*).

When coil 101 is further, continuously inserted, then, as shown in FIG. 8(*c*), coil 101 further flexes in an increased amount. This flexure stores elastic energy in coil 101 and accordingly, coil 101 is inserted into cerebral aneurysm 133 with increased insertion force. When coil 101 is further inserted, then, as shown in FIG. 8(*d*), coil 101 rotates at a point in time. As a result of coil 101 having rotated in cerebral aneurysm 133, coil 101 contacts the aneurysmal wall at a restraint point 137, and restraint point 137 thus becomes a further restraint point to restrain coil 101. At the time, the elastic energy of coil 101 is released, and the insertion force exerted to insert coil 101 rapidly decreases.

In other words, the FIG. 6 graph shows insertion force increased/decreased in a sawtooth manner, which is caused as coil 101 is partially restrained by a wall portion or the like of cerebral aneurysm 133. While coil 101 is restrained at restraint point 136, coil 101 delivered through the tip of child catheter 102 more flexes, as shown in FIG. 8(*c*), and the insertion force exerted to insert coil 101 increases. Furthermore, as the insertion force increases, coil 101 rotates, as shown in FIG. 8(*d*), and at that time, the insertion force rapidly decreases. This phenomenon arises because coil 101 moves slowly and accordingly, coil 101 contacts the aneurysmal wall with static friction caused, and by the static frictional force, a portion of coil 101 is restrained by the aneurysmal wall.

Figure 9:
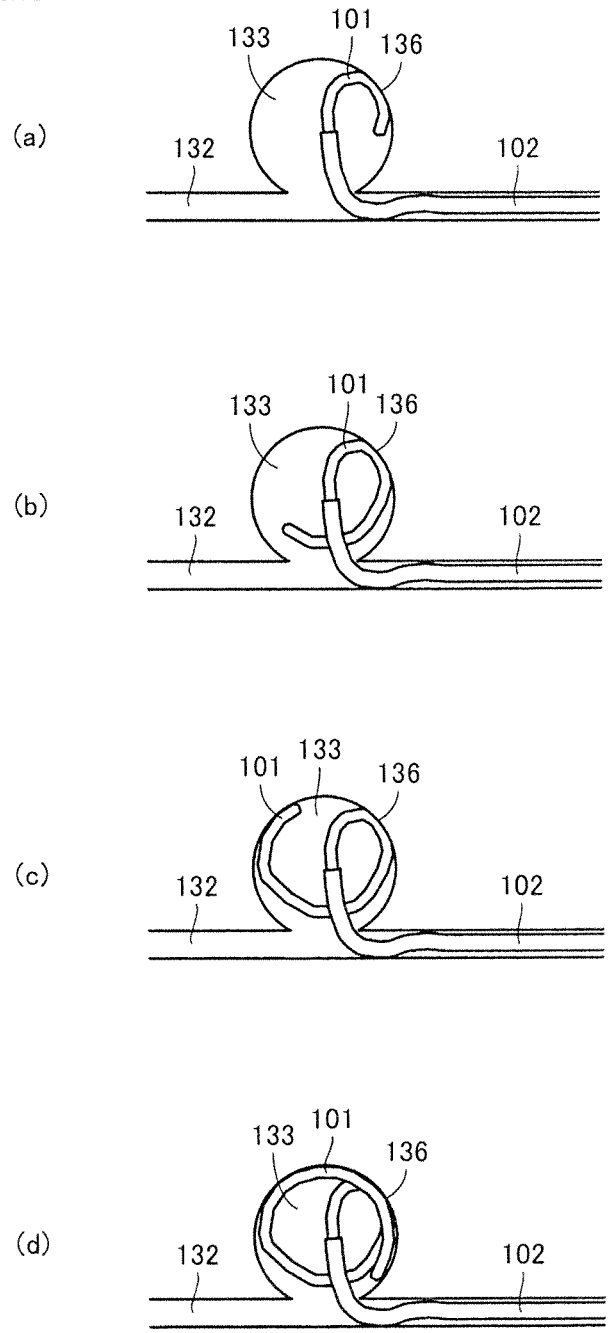
FIG. 9 schematically shows how the coil behaves in the simulated cerebral aneurysm when the coil is inserted into the simulated cerebral aneurysm at a rate of 1.0 mm/s.

On the other hand, FIG. 9 schematically shows how the coil behaves in the simulated cerebral aneurysm when the coil is inserted in the simulated cerebral aneurysm at a rate of 1.0 mm/s. FIG. 9(*a*) shows coil 101 in contact with the aneurysmal wall, and in that condition, coil 101 is further inserted. Only limited frictional force is caused between coil 101 and the aneurysmal wall, and coil 101 is inserted as it is, as shown in FIG. 9(*b*). Then, as shown in FIGS. 9(*c*) and 9(*d*), with only limited insertion resistance caused, coil 101 is not flexed and for example for a helical coil the coil maintains its original helical form and is thus inserted into cerebral aneurysm 133 as it is.

In other words, when coil 101 is inserted at a rate of 1.0 mm/s, the surface of the aneurysmal wall and that of coil 101 that contact each other maintain kinetic friction, as shown in FIG. 9, and coil 101 slides on the aneurysmal wall and is thus inserted into cerebral aneurysm 133. The phenomenon caused for the FIG. 8 insertion rate of 0.5 mm/s does not arise. Accordingly, as shown in FIG. 7, insertion force increasing/decreasing in a less sawtooth manner, as seen generally, is provided, and coil 101 can be inserted into cerebral aneurysm 133 with small insertion force on average.

While FIGS. 6-9 results are obtained with a simulated cerebral aneurysm of silicone resin used, it is imaginable that when coil 101 is inserted in vivo it is better used in a kinetic friction area. When the mean rate of table 1 is also considered, it is desirable to insert coil 101 into cerebral aneurysm 133 by moving coil 101 at a rate equal to or larger than 1.0 mm/s. In other words, it is desirable that drive device 1 moves delivery wire 104 in a direction at a rate of 1 mm/s to 4 mm/s to insert delivery wire 104 into blood vessel 132.

Figure 10:
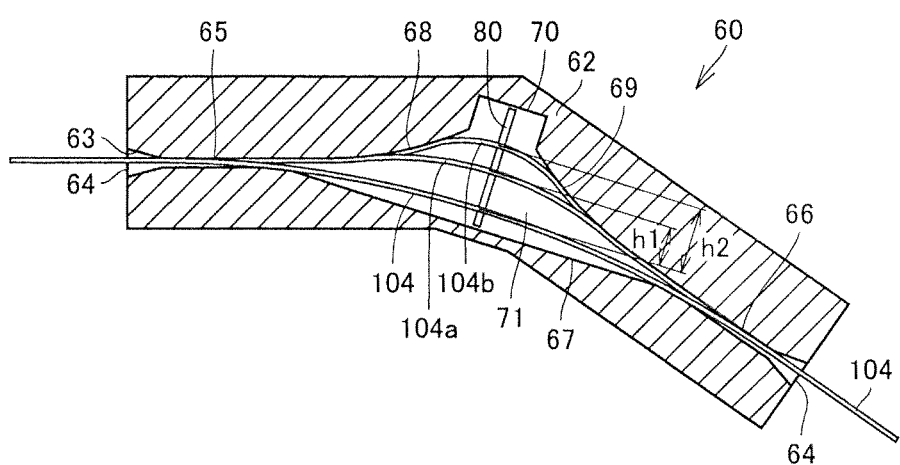
FIG. 10 shows how an insertion force sensor is configured, as seen in a schematic cross section.

Returning to FIG. 1, Y connector 31 has an insertion force sensor 60 incorporated therein. Delivery wire 104 experiences longitudinally compressive force (i.e., insertion force exerted in inserting delivery wire 104), which is measured with a measurement device configured including insertion force sensor 60. FIG. 10 is a schematic cross section of the insertion force sensor in configuration. As shown in FIG. 10, insertion force sensor 60 includes a sensor main body 62 having a through hole 63 allowing delivery wire 104 or a similar flexible medical linear body to pass therethrough. Delivery wire 104 passes through through hole 63 formed through sensor main body 62.

Through hole 63 is provided at its inlet and outlet letting in and out delivery wire 104 with a tapered input/output port 64 to increase the inlet and outlet in dimension to facilitate inserting delivery wire 104. Through hole 63 is formed to have opposite ends with restraint portions 65, 66 to restrain delivery wire 104 from moving in a direction other than its longitudinal direction. In sensor main body 62 at restraint portions 65, 66 through hole 63 has a diameter slightly larger than that of delivery wire 104 (e.g., 105% to 120% of that of delivery wire 104), and through hole 63 as seen along the longitudinal direction of delivery wire 104 has a length at least several times the diameter of delivery wire 104. Delivery wire 104 is thus restrained at restraint portions 65, 66 from moving in a direction other than its longitudinal direction.

When delivery wire 104 experiences longitudinally compressive force, sensor main body 62 defines a direction in which delivery wire 104 is curved in through hole 63. More specifically, through hole 63 is curved between restraint portions 65 and 66, and when delivery wire 104 passes through through hole 63, it is curved. Furthermore, through hole 63 between its two restraint portions 65 and 66 is formed to have internal walls 68 and 69 spaced away from an internal wall 67 to increase through hole 63 in diameter to form a space 71. Internal walls 68 and 69 outer than delivery wire 104 curved are widened to form space 71. In space 71, delivery wire 104 is not restrained from moving in a direction parallel to the plane of the drawing. Delivery wire 104 is bent in space 71 and thus passes through sensor main body 62.

At input/output port 64 and in space 71, through hole 63 as seen in a direction perpendicular to the plane of the drawing has a height slightly larger than the diameter of delivery wire 104 (e.g., 105% to 120% of the diameter of delivery wire 104), and delivery wire 104 is thus restrained from moving in the direction perpendicular to the plane of the drawing. In other words, at input/output port 64 and in space 71, through hole 63 is rectangular in a cross section perpendicular to the longitudinal direction of delivery wire 104. These define a direction in which delivery wire 104 is curved in through hole 63, and delivery wire 104 is positioned to determine a height of a ridge of a curvature of a curved portion of delivery wire 104 experiencing longitudinally compressive force (i.e., a maximum value of the distance from internal wall 67 to delivery wire 104).

In space 71, a line sensor 80 is disposed to traverse a cross section of through hole 63 in space 71. Line sensor 80 traverses an interior of space 71 from internal wall 67 of through hole 63 across an interior of a recess 70 configuring an internal wall of through hole 63 opposite to internal wall 67, as will be described hereinafter. Line sensor 80 is disposed in sensor main body 62 at space 71 along a locus of a vertex of a ridge of a curvature of delivery wire 104 curved when it experiences longitudinally compressive force.

Figure 11:
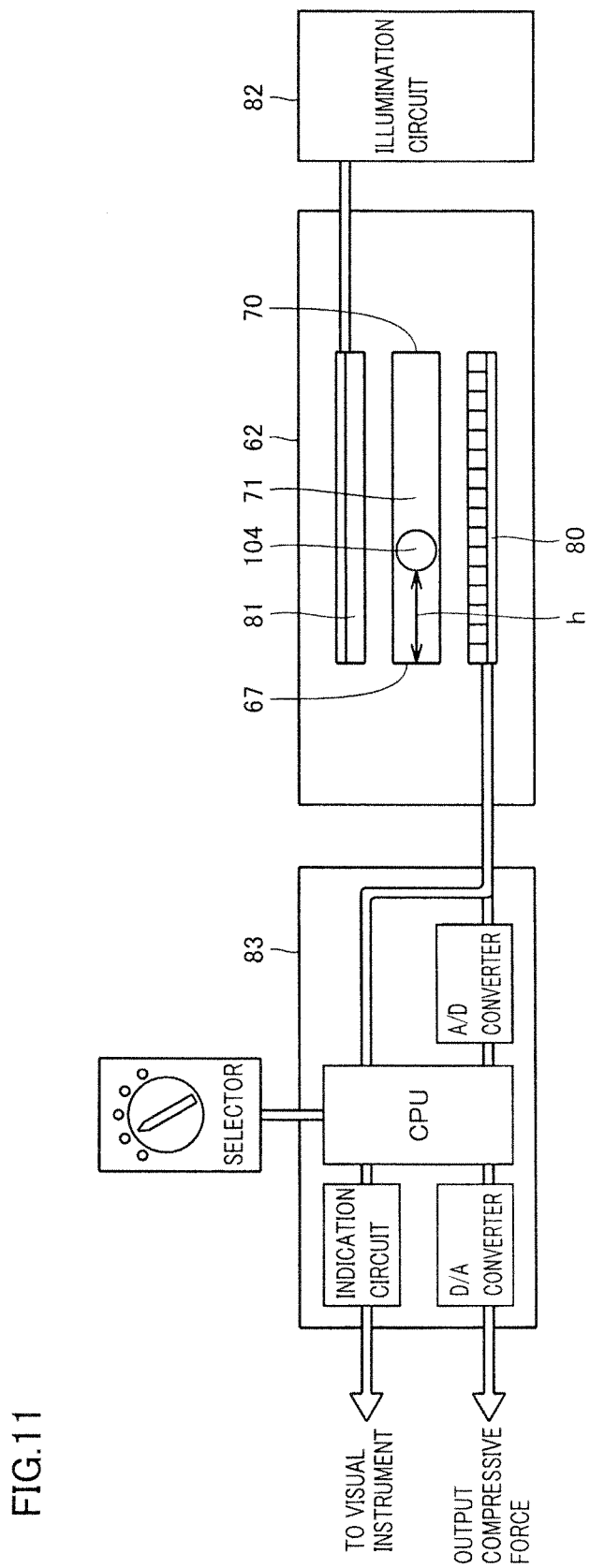
FIG. 11 is a schematic cross section of an optical system detecting at what degree a linear body is curved when the linear body penetrates the insertion force sensor.

FIG. 11 is schematic cross section of an optical system detecting a degree of a curvature of a linear body passed through the insertion force sensor. As shown in FIG. 11, sensor main body 62 has a light source 81 disposed therein to emit light. Furthermore, sensor main body 62 has disposed therein a line sensor 80 serving as a photoreceptor receiving light emitted by light source 81, i.e., a one-dimensional, optical array sensor having a plurality of photoreceptive elements, aligned in a single line. Internal to sensor main body 62, an optical path extending from light source 81 to line sensor 80 is formed of a transparent material transmitting light used for detection.

Light source 81 and line sensor 80 are positioned opposite to each other with delivery wire 104 posed therebetween and to also sandwich space 71 formed between two restraint portions 65 and 66. Light source 81 and line sensor 80 are disposed along a direction transverse to the longitudinal direction of delivery wire 104 and in the same direction as a direction in which delivery wire 104 curves when it experiences longitudinally compressive force. Line sensor 80 is disposed in a direction perpendicular to a direction in which internal wall 67 extends, and line sensor 80 is disposed to be orthogonal to delivery wire 104 (104*a*, 104*b*) at a vertex of a ridge of a curvature of delivery wire 104.

Furthermore, an illumination control circuit 82 and a conversion circuit 83 are provided external to sensor main body 62. Illumination control circuit 82 causes light source 81 to emit light. Conversion circuit 83 converts a degree of a curvature of delivery wire 104 detected from a quantity of light received by line sensor 80 relative to that of light emitted by light source 81 into longitudinally compressive force exerted to delivery wire 104, and outputs it. Conversion circuit 83 may have an amplification circuit amplifying an output of line sensor 80.

When delivery wire 104 experiences longitudinally compressive force, the measurement device specifically operates, as described hereinafter. When delivery wire 104 experiences compressive force, delivery wire 104 is curved in through hole 63 at space 71, and as the compressive force increases, delivery wire 104 is curved with its curvature's ridge increased in height, i.e., delivery wire 104 has an increased distance to internal wall 67. For example, as shown in FIG. 10, when compressive force p1 is exerted, a curvature is provided as indicated by delivery wire 104*a*, that is, a curvature is ridged to have a height increased by h1 compared with that provided when delivery wire 104 does not experience compressive force. Similarly, when compressive force p2 larger than p1 is exerted, a curvature is provided as indicated by delivery wire 104*b*, that is, a curvature is ridged to have a height increased by h2 compared with that provided when delivery wire 104 does not experience compressive force.

When delivery wire 104 is curved, it provides a ridge having some height, which can be sensed with line sensor 80. More specifically, when line sensor 80 receives light emitted by light source 81 positioned opposite to line sensor 80 with space 71 interposed, delivery wire 104 lying over a photoreceptive element of line sensor 80 interrupts the light emitted by light source 81, and the photoreceptive element receives a reduced quantity of light. By detecting the photoreceptive element's position, delivery wire 104 is positionally identified, and whether delivery wire 104 has a curvature with a ridge increased/decreased in height, i.e., in what degree delivery wire 104 is curved, can be detected.

Conversion circuit 83 shown in FIG. 11 can receive an output of each photoreceptive element of line sensor 80 and detect therefrom in what degree delivery wire 104 is curved, and based on a predetermined correlation between a height of a ridge of a curvature of delivery wire 104 and compressive force exerted to delivery wire 104 (e.g., amounts h1 and h2 increased in the height of the ridge of the curvature of delivery wire 104 corresponding to compressive forces p1 and p2), the conversion circuit can convert the height of the ridge of the curvature of delivery wire 104 into compressive force exerted to delivery wire 104 and output it. Compressive force exerted to delivery wire 104 in its longitudinal direction can thus be measured. Note that to appropriately form an image of delivery wire 104 on line sensor 80, a lens, a slit, a filter interrupting external light, and/or a similar optical element may be set in the present optical system.

Furthermore, as shown in FIG. 10, internal walls 68 and 69 configuring a wall surface of space 71 are formed to be curved and thus convexed toward an inner side of through hole 63. As shown in FIG. 10, internal wall 68 is formed to have a curved surface that contacts an internal wall of through hole 63 at restraint portion 65 and internal wall 69 is formed to have a curved surface that contacts an internal wall of through hole 63 at restraint portion 66. Furthermore, in space 71 between internal walls 68 and 69, recess 70 is formed. Recess 70 is formed by recessing the internal wall of through hole 63 toward an outer side of sensor main body 62 so that in space 71 between internal walls 68 and 69 through hole 63 has an internal wall spaced from internal wall 67 farther.

Space 71 has a wall portion formed in a geometry of internal walls 68 and 69 each having a curved surface convexed toward the inner side of through hole 63, and recess 70 combined together. Space 71 thus shaped allows delivery wire 104 experiencing longitudinal compressive force to be curved therein internal to through hole 63 along an internal wall of through hole 63 that is located outer than the curvature of delivery wire 104 (i.e., internal walls 68 and 69). Furthermore, delivery wire 104 can partially be curved away from internal walls 68 and 69. Furthermore, as compressive force increases, points at which delivery wire 104 is away from internal walls 68 and 69, i.e., points of contact, are less distant from each other.

This can prevent delivery wire 104 from buckling in space 71. More specifically, delivery wire 104 that buckles with a small load can also be curved in space 71 without buckling, and in what degree delivery wire 104 is curved can be detected with precision. The degree of the curvature detected can be converted to measure longitudinally compressive force exerted to delivery wire 104.

Furthermore, space 71 having recess 70 allows compressive force exerted to delivery wire 104 to be measured with precision over a wide range. More specifically, compressive force exerted to delivery wire 104 is measured by detecting a height of a ridge of a curvature of delivery wire 104 in space 71. In doing so, compressive force exerted to delivery wire 104 can be measured when a vertex of the curvature of delivery wire 104 in space 71, i.e., a point of delivery wire 104 in space 71 that is remotest from internal wall 67, is not in contact with any internal wall of space 71. With recess 70 provided, bringing the vertex of the curvature of delivery wire 104 into contact with an internal wall of space 71 will require larger longitudinally compressive force. Compressive force exerted to delivery wire 104 can thus be measured across an increased range.

Furthermore, for each of various types of delivery wires 104 having different Young's moduli or different cross sections, a correlation between compressive force and height of ridge of curvature can previously be measured and stored in the conversion circuit and which correlation should be used can be selected in accordance with which delivery wire 104 is used. Insertion force sensor 60 can thus be provided that is capable of measuring longitudinally compressive force exerted to delivery wire 104 regardless of whether delivery wire 104 buckles with a large or small load, and a single insertion force sensor 60 can be applied economically to delivery wires 104 formed of a variety of materials and having different diameters.

Figure 12:
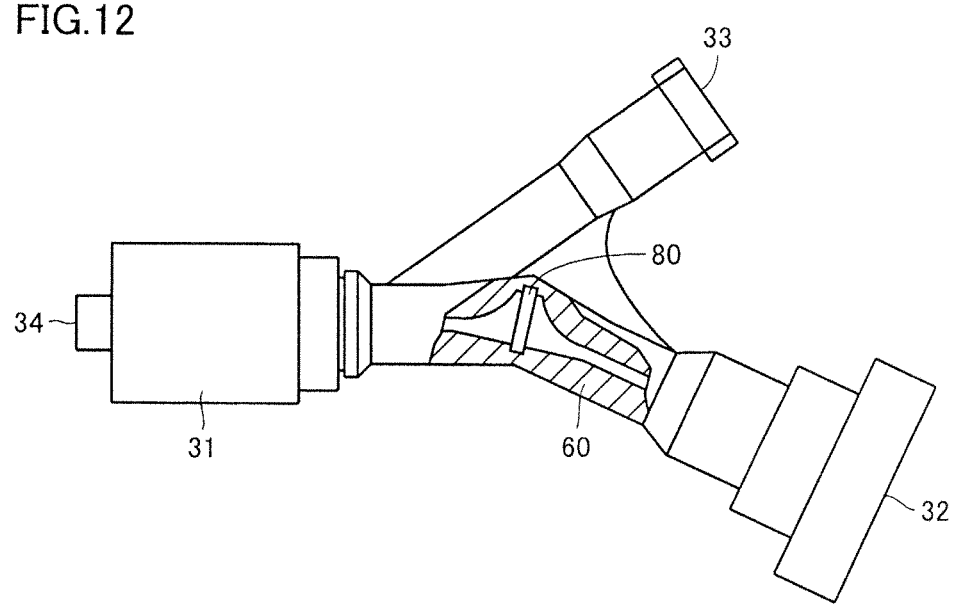
FIG. 12 schematically shows the insertion force sensor incorporated in a Y connector and thus used by way of example.

FIG. 12 schematically shows the insertion force sensor incorporated in a Y connector and thus used by way of example. As shown in FIG. 12, Y connector 31 serving as another medial instrument having insertion force sensor 60 incorporated therein includes input port 32, another input port 33, and output port 34. Insertion force sensor 60 is incorporated in Y connector 31 at a passage communicating between input port 32 and output port 34. Delivery wire 104 is guided to a target site in a body through an operation performed through input port 32.

Insertion force sensor 60 can be used to measure how longitudinally compressive force exerted to the medical linear body inserted in a bodily vessel increases to measure a load exerted by the medical linear body to the bodily vessel as reaction force against compressive force. In other words, it can sense that the medical linear body has its tip in contact with an inner wall of the vessel. The bodily vessel can thus be prevented from experiencing excessive load.

In addition, as insertion force sensor 60 is incorporated in Y connector 31, delivery wire 104 can be operated through input port 32 of Y connector 31 while a drug can be injected through the other input port 33 of Y connector 31. For example, physiological saline can be injected through the other input port 33 to reduce friction between a catheter and a guide wire. In addition, for example, after a catheter inserted in a blood vessel is guided ex vivo to an in vivo target site, a contrast agent can be injected through the other input port 33 so that the contrast agent can reach the in vivo target site.

Insertion force sensor 60 measuring compressive force exerted to delivery wire 104 employs line sensor 80 that is an optical sensor. The optical sensor allows a transparent resin material or a similar transparent material to be disposed between light source 81 and space 71 and between line sensor 80 and space 71, as shown in FIG. 11. Sensor components such as light source 81 and line sensor 80 can be incorporated internal to sensor main body 62, and the sensor components are not exposed to space 71. The sensor components can thus be prevented from exposure to liquid such as physiological saline injected through the Y connector 31 other input port 33. This can eliminate the necessity of considering a possibility that the sensor components may be exposed to liquid and thus fail or have a similar defect. This can facilitate cleaning or disinfecting Y connector 31 having insertion force sensor 60 incorporated therein.

A compressive force informing device that outputs compressive force detected via insertion force sensor 60 and informs the operator thereof is representatively a visual instrument indicating the compressive force that insertion force sensor 60 senses numerically or in a meter or a graph, an audio instrument converting compressive force to a sound corresponding thereto, and/or the like. The insertion device of the present embodiment can include one of the visual and audio instruments or both of them.

As shown in FIG. 1, insertion force sensor 60 has a sensor output control device 90 electrically connected thereto via a line 91 to control an output of the visual instrument and that of the audio instrument. FIG. 1 exemplarily shows an indicator 93 serving as a visual instrument indicating an output in voltage of insertion force sensor 60 that is converted to compressive force exerted to delivery wire 104 and is thus represented numerically. Furthermore, FIG. 1 also exemplarily shows an audio instrument outputting through a speaker 92 an alarming sound that varies its audio effect when insertion force sensor 60 outputs voltage equal to or larger than a predetermined threshold value, i.e., when delivery wire 104 experiences compressive force equal to or larger than a predetermined threshold value.

During a coil embolization treatment, a doctor pays his/her attention to a radioscopic image of cerebral aneurysm 133 and coil 101. Accordingly, it is convenient to use the audio instrument to audibly inform the doctor of compressive force exerted to delivery wire 104 as it is driven by drive device 1. For example, when delivery wire 104 experiences compressive force exceeding the predetermined threshold value, an alarming sound can be generated, and as compressive force increases, the alarming sound can be changed stepwise in tone (such as intermittent and continuous sounds, high and low sounds, and the like).

Furthermore, whether delivery wire 104 experiences longitudinally compressive force equal to or larger than the predetermined threshold value or not can also be presented to the doctor by varying a visual effect utilizing light. For example, when compressive force exceeds the predetermined threshold value, a level meter, an alarm light and/or the like can be turned on. Furthermore, a lamp may emit light varying in color around the predetermined threshold value. As compressive force increases, a lamp may emit light varying in color stepwise or flash on and off at a rate varying stepwise. Speaker 92 and the lamp may be used together. Furthermore, a visual or sound effect rapidly changed around a threshold value is further effective as it ensures drawing the doctor's attention.

The visual, audio and/or similar instruments that output an alarming sound, turn on a lamp and/or the like ensure that the doctor recognizes when delivery wire 104 experiences longitudinally compressive force equal to or larger than a threshold value. This can help a doctor who performs a coil embolization treatment to alone manipulate both child catheter 102 and delivery wire 104 without exerting excessive insertion force to delivery wire 104 and hence exerting an excessive load to cerebral aneurysm 133.

As has been described above, the present embodiment provides an insertion device inserting delivery wire 104 into human body 131 through blood vessel 132, that includes drive device 1 moving delivery wire 104 in its longitudinal direction and foot switches 41 and 46 outputting a signal to control starting/stopping drive device 1. This allows a doctor who manipulates child catheter 102 with delivery wire 104 inserted therethrough by hand to operate foot switches 41 and 46 with his/her loot to move delivery wire 104, and thus enhances the insertion device in operability. Child catheter 102 and delivery wire 104 can thus be manipulated by a singe doctor alone.

Furthermore the insertion device includes a measurement device measuring longitudinally compressive force exerted to delivery wire 104 and a compressive force informing device informing an operator of compressive force measured by the measurement device. This ensures that the doctor recognizes when coil 101 attached to the tip of delivery wire 104 exerts increased compressive force to cerebral aneurysm 133. This can prevent cerebral aneurysm 133 from experiencing an excessive load. In other words, this ensures that while child catheter 102 and delivery wire 104 are manipulated by a single doctor alone, coil 101 attached to the tip of delivery wire 104 can be prevented from exerting an excessive load to cerebral aneurysm 133, and the insertion device can thus be further enhanced in operability.

Furthermore, delivery wire 104 is longitudinally moved by drive device 1 including speed reducer 9 that receives a torque generated by motor 3, reduces the torque in speed and thus outputs it. This allows driving roller 5 to receive a torque increased in proportion to a speed reduction ratio. This in turn allows motor 3 small in size to be used to drive delivery wire 104 with increased force. Drive device 1 can be produced at a reduced cost and miniaturized. Motor 3 has its rotational speed controlled by the voltage applied thereto, and simply varying the voltage allows delivery wire 104 to be moved at an adjusted rate. Drive device 1 can be produced at a further reduced cost and enhanced in reliability.

Furthermore, motor 3 and speed reducer 9 are accommodated in a casing formed of housing 2 and partition wall 16 (i.e., small chamber 2b), with partition wall 16 provided with hole 16a receiving and passing therethrough rotary shaft 4 transmitting a torque from speed reducer 9 to driving roller 5. Hole 16a has an inner circumferential surface provided with seal 19 in contact with an outer circumferential surface, or a rotation surface, of rotary shaft 4 sealing the interior of small chamber 2b externally. The internal space of large chamber 2a having driving roller 5 and driven roller 6 accommodated therein can be isolated from that of small chamber 2b. Small chamber 2b can thus be prevented from having its internal space exposed to liquid that would otherwise enter from large chamber 2a. Motor 3 and speed reducer 9 can thus be waterproofed, which can facilitate cleaning and disinfecting large chamber 2a.

Furthermore, drive device 1 moves delivery wire 104 in a direction at a rate of 1 mm/s to 4 mm/s to insert delivery wire 104 into blood vessel 132. Drive device 1 that moves delivery wire 104 at a rate equal to or larger than 1 mm/s can minimize/prevent retention of coil 101 of the tip of delivery wire 104 relative to a wall portion of cerebral aneurysm 133. Coil 101 can be inserted into cerebral aneurysm 133 with small insertion force on average. Drive device 1 that moves delivery wire 104 at a rate equal to or smaller than 4 mm/s can facilitate moving delivery wire 104 and manipulating child catheter 102 in liaison.

Furthermore, driving roller 5 and driven roller 6 have rotation surface 5a and rotation surface 6a, respectively, formed of an elastic material. Furthermore, the driving roller 5 rotation surface 5a is provided with feed groove 5b, and delivery wire 104 is displaced in feed groove 5b. This can increase frictional force caused between rotation surfaces 5a, 6a and delivery wire 104 pinched therebetween, and thus minimize/prevent slippage of delivery wire 104 relative to rotation surface 5a and rotation surface 6a while delivery wire 104 is moved.

In the above description, an insertion device has been described that inserts into human body 131 through blood vessel 132 delivery wire 104 having a tip with coil 101 attached thereto for an embolization treatment to embolize cerebral aneurysm 133. The present insertion device may be any insertion device that can guide a flexible linear medial instrument in the form of a medical linear body into a blood vessel, a ureter, a bronchus, a lymphatic vessel, a digestive tract or a similar bodily vessel and allows it to be manipulated ex vivo and thus guided to a target site. For example, the medical linear body may be a catheter or a guide wire.

Although the present invention has been described and illustrated in embodiments in detail, it is clearly understood that the same is by way of illustration and example only and is not to be taken by way of limitation. The scope of the present invention is defined by the terms of the claims, rather than the description above, and is intended to include any modifications within the scope and meaning equivalent to the terms of the claims.

DESCRIPTION OF THE REFERENCE SIGNS

1: drive device, 2: housing, 2a: large chamber, 2b: small chamber, 3: motor, 4: rotary shaft, 5: driving roller, 5a, 6a: rotation surface, 5b: feed groove, 6: driven roller, 7: supporting member, 8: elastic body, 9: speed reducer, 10: lid member, 11: hinge, 12: lever, 13: projection, 14: engagement portion, 15: elastic portion, 16: partition wall, 16a: hole, 17: guide groove, 18: raised portion, 19: seal, 31: Y connector, 32, 33: input port, 34: output port, 40: control circuit, 41: foot switch for insertion, 43: insertion rate control unit, 45, 50: volume switch, 46: foot switch for withdrawal, 48: withdrawal rate control unit, 60: insertion force sensor, 62: sensor main body, 63: through hole, 64: input/output port, 65, 66: restraint portion, 67, 68, 69 internal wall, 70: recess, 71: space, 80: line sensor, 81: light source, 82: illumination control circuit, 83: conversion circuit, 90: sensor output control device, 92: speaker, 93: indicator, 100: medial instrument, 101: coil, 102: child catheter, 103: parent catheter, 104, 104a, 104b: delivery wire, 105, 106: holding portion, 111, 121: Y connector, 112, 122: input port, 131: human body, 132: blood vessel, 133: aneurysm, 134: area having a coil densely, 135: area having a coil less densely, 136: restraint point, 137: restraint point.

The invention claimed is:

1. An insertion device for inserting a medical linear body into a bodily vessel, comprising:
 a drive device operative to move said medical linear body in a longitudinal direction thereof;
 a foot switch operative for generating and outputting a signal to control starting/stopping said drive device;
 a medical instrument further comprising a measurement device operative to measure longitudinally compressive force exerted to said medical linear body, wherein the medical instrument comprises a through hole capable of receiving and allowing said medical linear body to pass therethrough and wherein said measurement device includes a sensor operative to sense a degree of a curvature of said medical linear body; and a conversion circuit operative for converting said degree of said curvature of said medical linear body sensed by said sensor into the compressive force exerted to said medical linear body; and a compressive force informing device operative for informing an operator of the compressive force exerted to said medical linear body, wherein said drive device comprises:
  a torque generator,
  a driving roller providing rotational motion by a torque generated by said torque generator,
  a driven roller providing rotational motion as said driving roller rotates,
  a speed reducer posed between said torque generator and said driving roller, and receiving the torque from said torque generator, reducing the torque in speed, and outputting the torque reduced in speed,
  a housing surrounding an internal space of the drive device, wherein said housing comprises a partition wall sectioning the internal space of the housing into a first space accommodating the driving roller and the driven roller therein and a second space accommodating the torque generator and the speed reducer therein, wherein the housing comprises a securing portion for securing at least a portion of the medical instrument within the housing, and
  a rotary unit operative for transmitting the torque from said speed reducer to said driving roller, said driving roller and said driven roller having a rotation surface and a rotation surface, respectively, cooperating to pinch said medical linear body, wherein the partition wall of said housing comprises a hole for receiving and passing said rotary unit therethrough, said hole having an inner circumferential surface provided with a seal in contact with an outer circumferential surface of said rotary unit and sealing an interior of the second space of said housing externally.

2. The insertion device according to claim 1, wherein said medical linear body is any of a catheter, a guide wire, and a delivery wire having a tip with a coil attached thereto for embolization.

3. The insertion device according to claim 1, wherein:
  said foot switch includes a foot switch for insertion and a foot switch for withdrawal; and
  said foot switch for insertion is operated to cause said drive device to operate to move said medical linear body in a direction to insert said medical linear body into the vessel;
  said foot switch for withdrawal is operated to cause said drive device to operate to move said medical linear body in a direction to withdraw said medical linear body from the vessel.

4. The insertion device according to claim 1, wherein said compressive force informing device includes at least one of a visual instrument visually indicating the compressive force exerted to said medical linear body, and an audio instrument converting the compressive force exerted to said medical linear body into a sound corresponding thereto.

5. The insertion device according to claim 1, wherein said torque generator is an electric motor having a rotational speed controlled by voltage applied to said electric motor.

6. The insertion device according to claim 1, further comprising a rate control unit capable of adjusting a rate applied to cause said drive device to move said medical linear body.

7. The insertion device according to claim 1, wherein said drive device moves said medical linear body at a rate of 1 mm/s to 4 mm/s in a direction to insert said medical linear body into the vessel.

8. The insertion device according to claim 1, wherein
  said drive device further includes an elastic body attached to said lid member;
  said lid member is provided with a lever operated to open/close said lid member;
  when said lid member is closed, said elastic body presses said lid member with elastic force, which presses and thus fixes said lever; and
  said lever is elastically deformed to open said lid member.

9. The insertion device according to claim 1, wherein said driving roller and said driven roller have said rotation surfaces formed of an elastic material.

10. The insertion device according to claim 1, wherein at least one of said driving roller and said driven roller has said rotation surface provided with a groove; and said medical linear body is disposed in said groove.

* * * * *